(12) United States Patent
Miller et al.

(10) Patent No.: US 10,392,470 B2
(45) Date of Patent: Aug. 27, 2019

(54) POLYESTER NANOGEL CORE STAR POLYMERS FOR DELIVERY OF THERAPEUTIC AGENTS

(71) Applicant: International Business Machines Corporation, Armonk, NY (US)

(72) Inventors: Robert D. Miller, San Jose, CA (US); Victoria A. Piunova, San Jose, CA (US); William C. Swope, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 265 days.

(21) Appl. No.: 15/334,492

(22) Filed: Oct. 26, 2016

(65) Prior Publication Data

US 2018/0112033 A1   Apr. 26, 2018

(51) Int. Cl.
| | |
|---|---|
| *A61K 9/00* | (2006.01) |
| *A61K 9/51* | (2006.01) |
| *A61K 31/122* | (2006.01) |
| *C08G 63/664* | (2006.01) |

(52) U.S. Cl.
CPC .......... *C08G 63/664* (2013.01); *A61K 9/0019* (2013.01); *A61K 9/0053* (2013.01); *A61K 9/5146* (2013.01); *A61K 31/122* (2013.01); *C08G 2210/00* (2013.01)

(58) Field of Classification Search
CPC ............... C08G 2210/00; C08G 63/664; C08J 2367/04; C08J 3/075
See application file for complete search history.

(56) References Cited

U.S. PATENT DOCUMENTS

| | | | |
|---|---|---|---|
| 6,127,481 A | 10/2000 | Janssen et al. | |
| 8,470,891 B2 | 6/2013 | Hedrick et al. | |
| 8,765,098 B2 | 7/2014 | Appel et al. | |
| 2011/0243848 A1* | 10/2011 | Appel | A61K 49/0036 424/9.1 |
| 2012/0070563 A1* | 3/2012 | Mitchell | A61L 31/16 427/2.25 |
| 2013/0011441 A1 | 1/2013 | Hollinger et al. | |
| 2014/0370064 A1 | 12/2014 | Lee et al. | |

OTHER PUBLICATIONS

Bank et al. ("Coenzyme Q10: Clinical Update and Bioavailability" Journal of Evidence-Based Complementary & Alternative Medicine 2011, 16(2) 129-137).*

(Continued)

*Primary Examiner* — Kortney L. Klinkel
(74) *Attorney, Agent, or Firm* — Michael R. Roberts

(57) ABSTRACT

Amphiphilic star polymers were prepared having superior loading properties for delivery of hydrophobic biologically active materials intended for use in medical, cosmetic, and other applications. The star polymers comprise a plurality block copolymer arms linked to a crosslinked polyester core. The monovalent arms comprise a peripheral poly(ethylene oxide) block (PEG block) and a polyester block, which is linked to the core. The sidechain substituents of the polyester block substantially improve the loading capacity of the star polymer for CoQ10 and other hydrophobic materials.

21 Claims, 5 Drawing Sheets

Coenzyme Q10

Loaded Star Polymer

(56) References Cited

OTHER PUBLICATIONS

Beal, et al., "Experimental Therapeutics in Transgenic Mouse Models of Huntington's Disease", Nature Reviews, Neuroscience, 2004, vol. 5, 373-384.

Bencherif, et al., "Cell-Adhesive Star Polymers Prepared by ATRP", Biomacromolecules 2009, 10, 1795-1803.

Chang, et al., "Regioselective Baeyer-Villiger lactonization of 2-substituted pyrrolidin-4-one. Synthesis of statine", Tetrahedron Letters 47 (2006) 4865-4870.

Fukukawa, et al., "Synthesis and Characterization of Core-Shell Star Copolymers for In Vivo PET Imaging Applications", Biomacromolecules, 2008, 9 (4), 1329-1339.

Georgiou, et al., "Synthesis, Characterization, and Evaluation as Transfection Reagents of Double-Hydrophilic Star Copolymers: Effect of Star Architecture", Biomacromolecules 2005, 6, 2990-2997.

Lapienis G., "Star-shaped polymers having PEO arms", Progress in Polymer Science 34 (2009) 852-892.

Lee, et al., "Nanogel Star Polymer Architectures: A Nanoparticle Platform for Modular Programmable Macromolecular SelfAssembly, Intercellular Transport, and Dual-Mode Cargo Delivery", Adv. Mater. 2011, 23, 4509-4515.

Miller, et al., "Water soluble, biodegradable amphiphilic polymeric nanoparticles and the molecular environment of hydrophobic encapsulates: Consistency between simulation and experiment", Polymer 79 (2015) 255-261.

Nijenhuis, et al., "Crosslinked poly(L-lactide) and poly(e-caprolactone)", Polymer, 1996, vol. 37, No. 13, 2783-2791.

Oh, et al., "Atom transfer radical polymerization in inverse miniemulsion: A versatile route toward preparation and functionalization of microgels/nanogels for targeted drug delivery applications", Polymer 50 (2009) 4407-4423.

Wang, et al., "Synthesis and evaluation of a star amphiphilic block copolymer from poly(epsilon-caprolactone) and poly(ethylene glycol) as a potential drug delivery carrier", Bioconjugate Chemistry, 2005, 16(2), 397-405.

Wiltshire, et al., "Degradable Core Cross-Linked Star Polymers via Ring-Opening Polymerization", Macromolecules 2006, 39 (13), 4282-4285.

Xiong, et al., "Synthesis of PEG-Armed and Polyphosphoester Core-Cross-Linked Nanogel by One-Step Ring-Opening Polymerization", Macromolecules, vol. 42, No. 4, 2009, 893-896.

* cited by examiner

Coenzyme Q10     Loaded Star Polymer

POLYESTER NANOGEL CORE STAR POLYMERS FOR DELIVERY OF THERAPEUTIC AGENTS

BACKGROUND

The present invention relates to the synthesis of nanogel core star polymers with improved loading of hydrophobic cargo, and more specifically, to nanogel core star polymers having pendant alkyl functionality for improved cargo loading.

Commercial interest exists in developing biocompatible, well-defined polymer-based particles for the in vivo delivery of exogenous functional medically useful materials (e.g., pharmaceuticals and/or imaging agents). Organic nanoparticle platforms under development for these purposes include liposomes, dendrimers, and micelles. Alternatively, star polymers having a unimolecular, globular, polymer architecture are an increasingly attractive class of organic nanoparticles for biomedical research purposes (e.g., see Bencherif, S. A., et al., Biomacromolecules 2009, 10, 1795-1803; Fukukawa, K.-I., et al., Biomacromolecules 2008, 9, 1329; and Georgiou, T. K., et al., Biomacromolecules 2005, 6, 2990).

While topographically similar to dendrimers, (i.e., having a high local density of polymeric arms, surface functionality and interstitial regions), star polymers lack the synthetic and structural limitations of dendrimers and the dynamic instability of micelles and liposomes. Nanogel star polymers, which have polymer "arms" connected to a cross-linked polymer core, in particular, offer a modular platform in which the nanoparticle size, the number of arms, the nature of the arms, the core, as well as inner functionality of the core and the end (peripheral) functionality of the arms can be selectively modified.

Of specific importance to biomedical applications is the development and characterization of poly(ethylene glycol) (PEG) functionalized star polymers. The high water solubility and low immunogenicity of PEG have made PEG the most recognized polymer composition for promoting increased circulation time and biocompatibility of nanoparticles in vivo. Owing to previous synthetic difficulties, there has been limited work done on PEG-based nanogel-core star polymers as a nanoparticle platform for drug delivery.

Thus, nanogel-core star polymers are desired having PEG-functionalized arms that exhibit high loading efficiencies with respect to hydrophobic therapeutic agents used in medical treatments and cosmetic applications.

SUMMARY

Accordingly, a nanogel star polymer is disclosed, comprising:
a crosslinked hydrophobic polyester core C';
6 to 50 independent linear block copolymer arms, each of the arms comprising i) a hydrophilic PEG block P' comprising a poly(ethylene oxide) chain and ii) a hydrophobic polyester block P''', a first end unit of the polyester block linked to the PEG block, a second end unit of the polyester block linked to the core C', wherein the polyester block P''' comprises an ester repeat unit of formula (2):

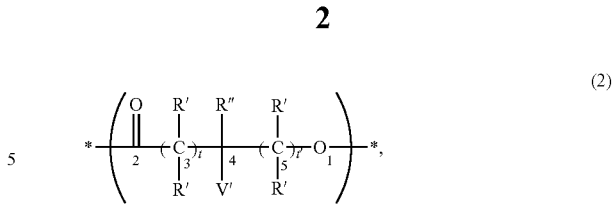

wherein
P''' has a polymer backbone that includes atomic centers numbered 1-5,
V' is a monovalent $C_3$-$C_{50}$ hydrocarbon radical,
each R' is an independent monovalent radical selected from the group consisting of hydrogen, methyl, and ethyl,
R'' is a monovalent radical selected from the group consisting of hydrogen and alkyl groups comprising 1 to 6 carbons,
t is a positive integer having a value of 0 to 5, and
t' is a positive integer having a value of 0 to 5.

Also disclosed is a loaded star polymer, comprising:
an above-described nanogel star polymer; and
a therapeutic agent used in treatment of cellular tissue;
wherein
the therapeutic agent is in contact with the polyester block P''' and/or the core.

An aqueous mixture comprising an above-described loaded star polymer, wherein the loaded star polymer is present as a particle in contact with water.

The above-described and other features and advantages of the present invention will be appreciated and understood by those skilled in the art from the following detailed description, drawings, and appended claims.

DETAILED DESCRIPTION

The invention is based on unimolecular nanogel star polymers, which have utility as carriers for the delivery of therapeutic agents used in a treatment in which the therapeutic agent contacts cellular tissue. Treatments include the administration of drugs for a medical condition, administration of imaging agents for diagnosis of a medical condition, and cosmetic treatments. Other treatments can be for disease prevention, as in the delivery of vitamins and other dietary supplements, sun-tan lotions, and the like.

The star polymers are preferably biodegradable and/or biocompatible. The term "biodegradable" is defined by the American Society for Testing and Materials as degradation caused by biological activity, especially by enzymatic action, leading to a significant change in the chemical structure of the material. For purposes herein, a material is biodegradable if it undergoes 60% biodegradation within 180 days in accordance with ASTM D6400.

Figure 1A:
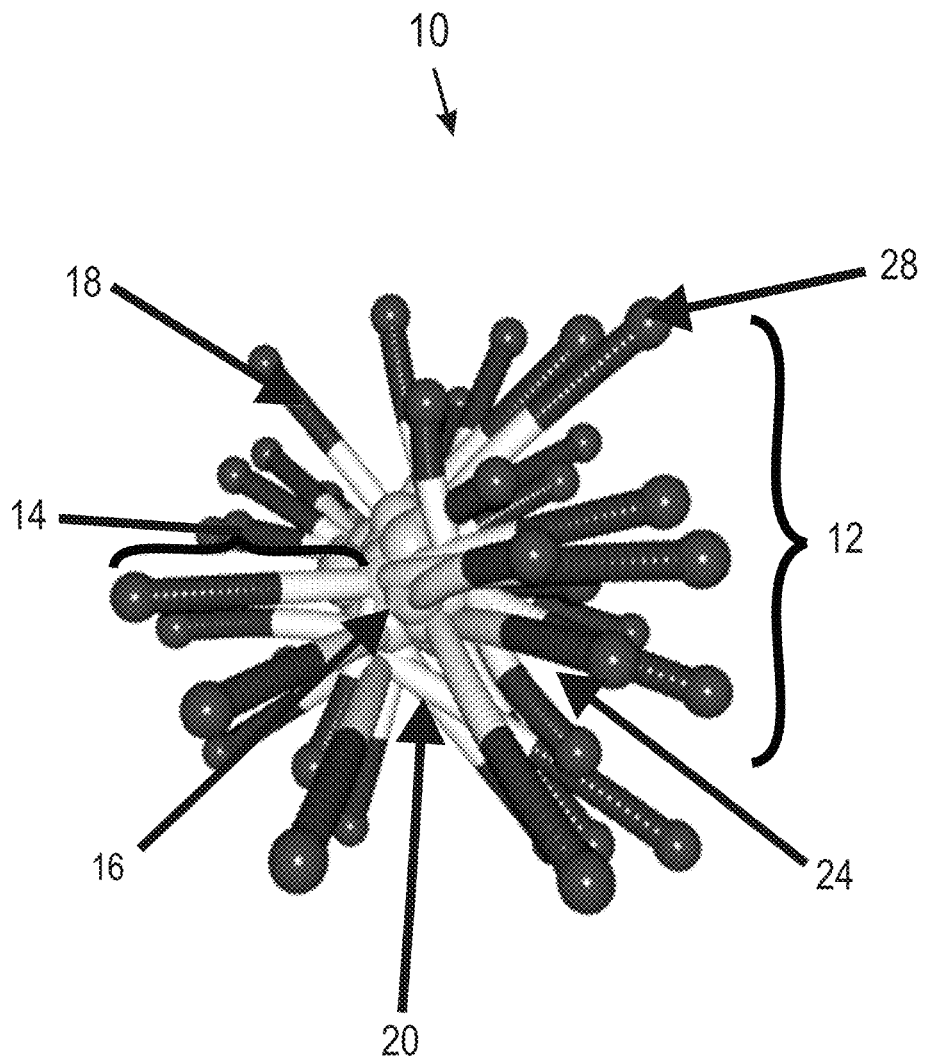
FIG. 1A is a 3-dimensional molecular model of an amphiphilic star polymer having a hydrophilic peripheral segment of the polymer arm and a hydrophobic inner segment.
Figure 1B:
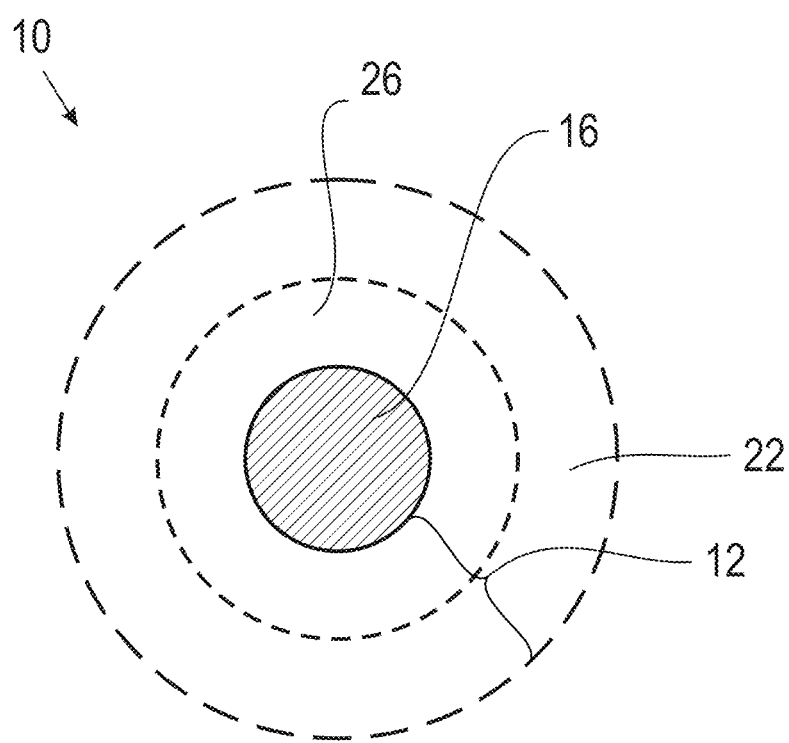
FIG. 1B is a cross-sectional view of a layer diagram of the amphiphilic star polymer of FIG. 1A, depicting the core shell structure, wherein the shell comprises an outer hydrophilic peripheral shell and a hydrophobic inner shell.

FIG. 1A and FIG. 1B are drawings illustrating a 3-dimensional representation of an exemplary disclosed star polymer macromolecule. Star polymer 10 comprises a shell 12 composed of six or more independent amphiphilic polymer arms 14, each of which is covalently linked to a central crosslinked polyester core 16. The polymer arms 14 comprise respective peripheral hydrophilic poly(ethylene oxide) blocks, referred to as PEG blocks 18 (P') and inner hydrophobic polyester blocks 20 (P'''), which are covalently linked to PEG blocks 18 by way of respective single bonds or divalent linking groups L' (not shown). Peripheral end groups 28 of polymer arms 18 are also indicated. Peripheral end groups 28 are linked to respective PEG blocks 18. Shell 12 has two regions, a hydrophilic outer shell region 22 (FIG. 1B) comprising PEG blocks 18 and interstitial region 24 (FIG. 1A), and a hydrophobic inner shell region 26 composed of the hydrophobic polyester blocks 20 and interstitial region 24. The dashed boundary lines around outer shell region 22 and inner shell region 26 of FIG. 1B indicate the interstitial area is shared by the outer and inner shell regions. The core 16 is preferably hydrophobic. Core 16 can be a living core, capable of initiating a polymerization or undergoing another chemical modification.

The star polymer macromolecule has a structure according to formula (1).

wherein
k is a positive number having an average value of 6 or more,
C' is a crosslinked polyester core having a valency of k,
E'-P'-L'-P'''-* is a monovalent block copolymer arm,
E' is a monovalent end group,
P' is a poly(ethylene oxide) block (PEG block),
L' is a single bond or a divalent linking group, and
P''' is a hydrophobic polyester block comprising an ester repeat unit of formula (2),

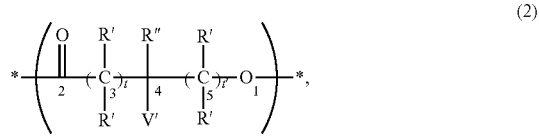

wherein
P''' has a polymer backbone that includes atomic centers numbered 1-5,
V' is a monovalent $C_3$-$C_{50}$ hydrocarbon radical,
each R' is an independent monovalent radical selected from the group consisting of hydrogen, methyl, and ethyl,
R'' is a monovalent radical selected from the group consisting of hydrogen and alkyl groups comprising 1 to 6 carbons, t is a positive integer having a value of 0 to 5, and
t' is a positive integer having a value of 0 to 5.

E' can be any suitable end group (e.g., methoxy, ethoxy, acetoxy). In an embodiment E' is methoxy. In another embodiment, at least one of t and t' is a positive integer greater than 0.

P' has a structure according to formula (3):

wherein n represents the degree of polymerization and is a positive number having an average value of 50 to 600. In an embodiment n has an average value of 80 to 200.

L' can be any suitable linking group with the proviso that the drug loading and drug release properties of the star polymers are not adversely affected. In an embodiment, L' is a single bond.

P''' can be a homopolymer, random copolymer, or block copolymer chain comprising the ester repeat unit.

In a particular embodiment, t is 2, t' is 2, each R' is hydrogen, and R'' is hydrogen of formula (2). That is, the ester repeat unit is a ring-opened form of a gamma-substituted epsilon-caprolactone. P''' can comprise 1 to 100, more preferably 10 to 50, and even more preferably 10 to 40 ester repeat units of formula (2).

Optionally, P''' can comprise other ester repeat units (diluent ester repeat units) for adjusting the amphiphilic properties of the arms. When a diluent repeat unit is present, P''' can comprise 0 to 100, more preferably 5 to 50, and even more preferably 5 to 40 of the diluent repeat units. As a non-limiting example, P''' can be a random copolymer or block copolymer of an ester repeat unit of formula (2) and a diluent ester repeat unit which is a ring-opened form of a lactone selected from the group consisting of ε-caprolactone, γ-butyrolactone, and combinations thereof.

Non-limiting exemplary V' groups include propan-1-yl (n-propyl), propan-2-yl (iso-propyl), butan-1-yl (n-butyl), butan-2-yl (sec-butyl), 2-methylpropan-1-yl (iso-butyl), 1,1-dimethylethan-1-yl (tert-butyl), pentan-1-yl (n-pentyl), pentan-2-yl (sec-pentyl), pentan-3-yl, 3-methylbutan-1-yl (iso-pentyl), 2,2-dimethylpropan-1-yl (neo-pentyl), 1,1-dimethylpropan-1-yl (tert-pentyl), hexan-1-yl, hexan-2-yl, hexan-3-yl, 4-methylpentan-1-yl, 3,3-dimethylbutan-1-yl, 2,2-dimethylbutan-1-yl, 1,1-dimethylbutan-1-yl, 3,3-dimethylbutan-2-yl, 1,3-dimethylbutan-2-yl, heptan-1-yl, heptan-2-yl, heptan-3-yl, heptan-4-yl, 5-methylhexan-1-yl, 4-methylhexan-1-yl, 3-methylhexan-1-yl, 2-methylhexan-1-yl, 4,4-dimethylpentan-1-yl, 3,3-dimethylpentan-1-yl, 2,2-dimethylpentan-1-yl, 4,4-dimethylpentan-2-yl, 3,3-dimethylpentan-2-yl, 3,4-dimethylpentan-2-yl, 3,3,2-trimethylbutan-1-yl, 3,2,2-trimethylbutan-1-yl, 3-methyl-1,1-dimethyl-butan-2-yl, octan-1-yl, diisopropylmethyl, cyclopentyl, cyclohexyl, norbornyl, and adamantyl.

Ring Opening Polymerization (ROP)

The following description of ROP methods applies to the formation of the polyester block P''' and the core.

The star polymers can be prepared in one or more reaction vessels by organocatalyzed ROP of cyclic ester monomer(s) (lactones). Preferably, the polymer arms are formed first using one or more sequential ROPs in which the first ROP is initiated by a mono-nucleophilic polymeric initiator, which is a precursor for the P' block and comprises a poly(ethylene oxide) chain. These polymer initiators are referred to herein generally as "PEG initiators". The reaction mixture comprises a PEG initiator, a solvent, an organocatalyst, an optional accelerator, and a first cyclic ester monomer. The first cyclic ester monomer comprises a V' group and is capable of a ring opening reaction to produce an ester repeat unit of formula (2). Agitating the reaction mixture at a temperature of 15° C. to 150° C. effects ring opening polymerization of the first cyclic ester monomer, thereby forming a precursor arm. The precursor arm is a linear block copolymer comprising a PEG block P' covalently linked to a polyester block P''', wherein P''' comprises an ester repeat unit of formula (2). The polyester block P''' has a nucleophilic terminal alcohol group capable of initiating another ROP.

Herein, a "linear" polymer macromolecule has one polymer backbone connecting two polymer ends, as opposed to a branched polymer macromolecule having two or more intersecting polymer backbones and three or more polymer ends. Herein, a polymer backbone is the collection of atomic centers providing the shortest path of covalent bonds from one polymer end to an opposing polymer end. The polymer backbone can include atomic centers of one or more polymer chain portions joined by respective linking groups. A given polymer chain portion can be a homopolymer, random copolymer, or block copolymer chain of the repeat units thereof. The atomic centers of the polymer backbone can include one or more atomic centers of the linking groups joining the polymer chain portions. Thus, the precursor arm is a linear block copolymer macromolecule, and an arm of the star polymer is a linear block copolymer portion of the star polymer macromolecule. The star polymer macromolecule is not a linear polymer macromolecule.

The ROP reaction mixture can comprise one or more diluent cyclic ester monomers. In this instance, the polyester block P''' can be a random copolymer of repeat units derived from the first cyclic ester and the one or more diluent cyclic ester monomers. Alternatively, ROP polymerizations of two or more cyclic ester monomers that include a first cyclic ester monomer can be conducted sequentially, in any order, with the resulting polyester block P''' being a block copolymer chain comprising as many polyester blocks as sequential ROPs. At least one of the polyester blocks contains an ester repeat unit of formula (2).

The crosslinked core is preferably prepared by one or more sequential ROPs initiated by the precursor arms. Crosslinking is accomplished using a multi-functional cyclic ester (i.e., a compound comprising two or more cyclic ester groups capable of ring opening polymerization), optionally in combination with one or more non-crosslinking monofunctional cyclic ester comonomers. The core-forming ROP effectively links 6 or more precursor arms to a single globular crosslinked polyester core, thereby forming a star polymer macromolecule. Optional non-crosslinking monofunctional cyclic ester monomers include those of formula (4) having a V' substituent. The mono-functional cyclic ester comonomer can serve to adjust crosslink density, hydrophobicity, and swelling properties of the core in a given solvent.

The cyclic ester monomers can undergo ring-opening polymerization (ROP) to form biodegradable polymers of different tacticities. Atactic, syndiotactic and isotactic forms of the polymers can be produced that depend on the cyclic ester monomer(s), its isomeric purity, and the polymerization conditions.

The star polymers and any component used to prepare the star polymers can be stereospecific or non-stereospecific. As examples, a stereospecific monomer and/or stereospecific repeat unit i) has a non-superposable mirror image and ii) comprises one or more asymmetric tetravalent carbons (i.e., tetrahedral $sp^3$ carbons). Each asymmetric tetravalent carbon is assigned an R or S symmetry based on Cahn-Ingold-Prelog (CIP) symmetry rules. If, for example, a stereospecific repeat unit has one asymmetric tetravalent carbon, then the stereospecific repeat unit can be present substantially as the R stereoisomer or substantially as the S stereoisomer, meaning the stereoisomer can be present in a stereoisomeric purity of 90% to 100%, 94% or more, or more particularly 98% to 100%. In another example, if the stereospecific repeat unit has two asymmetric tetravalent carbons, the stereospecific repeat unit can be present substantially as the R,R stereoisomer, substantially as the R,S stereoisomer, substantially as the S,S stereoisomer, or substantially as the S,R stereoisomer.

Scheme 1 illustrates the preparation of a biodegradable star polymer by a two-step ring opening polymerization (in Examples 2 and 7 further below). The precursor arm is prepared first and isolated prior to the ROP to form the core.

Scheme 1

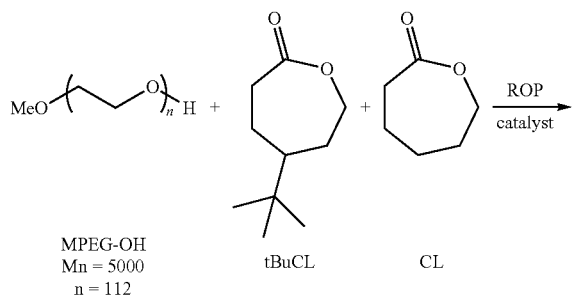

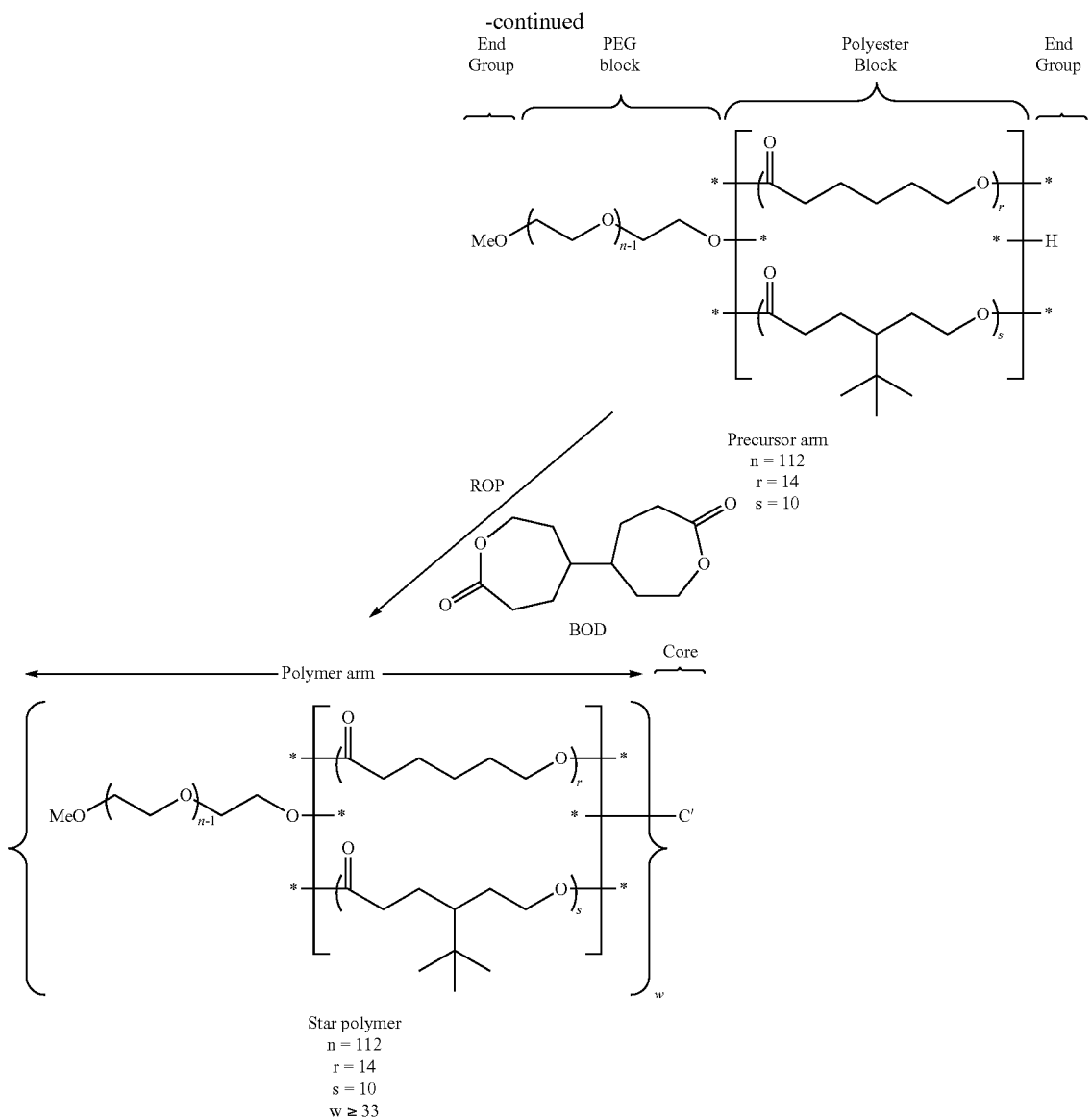

Precursor arm
n = 112
r = 14
s = 10

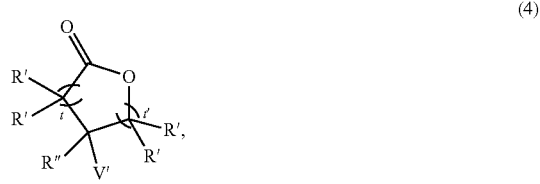

Star polymer
n = 112
r = 14
s = 10
w ≥ 33

The square brackets in the above structures enclose a polymer chain (polyester block P'''). Vertical stacking of the ester repeat units within the square brackets indicates a random distribution of the ester repeat units within the polymer chain (i.e., the polyester block P''' is a random copolymer of the ester repeat units). The curly braces of the star polymer enclose the polymer arms. C' is the crosslinked core, which in this example is formed from BOD. C' also has a valency of w, which in this example is 33 (i.e., the star polymer has 33 polymer arms linked to the core C').

For simplicity, all examples herein assume the ideal case that all initiating groups react and, therefore, the length of polymeric blocks may be described by the division of the number of moles of monomer units by the number of moles of initiating sites. However, the reaction of 100% of the initiating sites is not a requirement for successful implementation of the invention. Non-reacted nucleophilic initiating groups can serve as additional reaction or initiator sites during subsequent synthetic processes. Therefore, it is advantageous that a high percentage of the nucleophilic initiating groups undergo the ring opening reaction.

More specific details of the ROP reaction components and conditions are provided in the following sections.

Cyclic Ester Monomers

The first cyclic ester monomer can have a structure according to formula (4):

$$\text{(4)}$$

wherein
V' is a monovalent $C_3$-$C_{50}$ hydrocarbon radical,
each R' is an independent monovalent radical selected from the group consisting of hydrogen, methyl, and ethyl, R" is a monovalent radical selected from the group consisting of hydrogen and alkyl groups comprising 1 to 6 carbons, t is a positive integer having a value of 0 to 5, and t' is a positive integer having a value of 0 to 5.

Non-limiting examples of cyclic ester monomers of formula (4) include those of List 1.

List 1

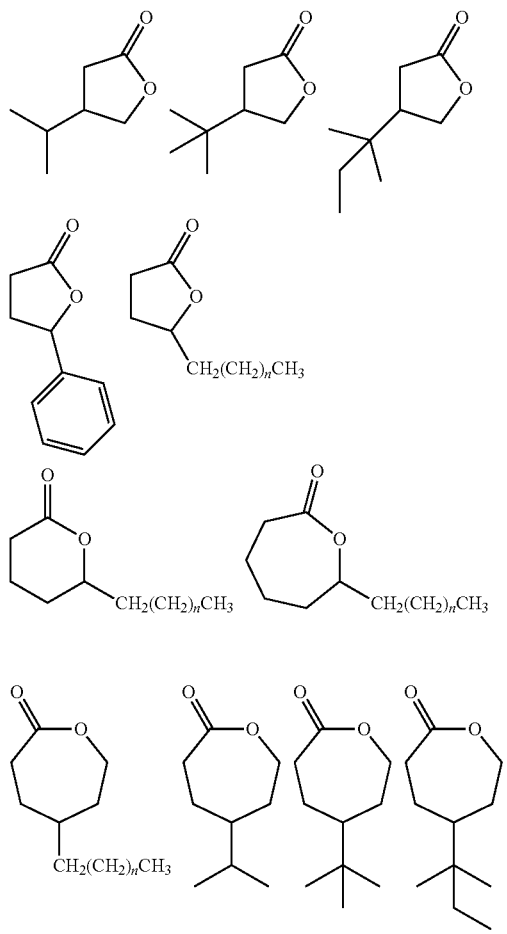

n = 1-10

Other first cyclic ester monomers can have a structure according to formula (5):

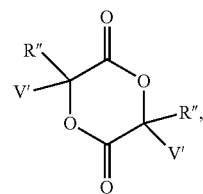

(5)

wherein

V' is a monovalent $C_3$-$C_{50}$ hydrocarbon radical, and

R" is a monovalent radical selected from the group consisting of hydrogen and alkyl groups comprising 1 to 6 carbons.

Non-limiting examples of cyclic ester monomers of formula (5) include those of List 2.

List 2

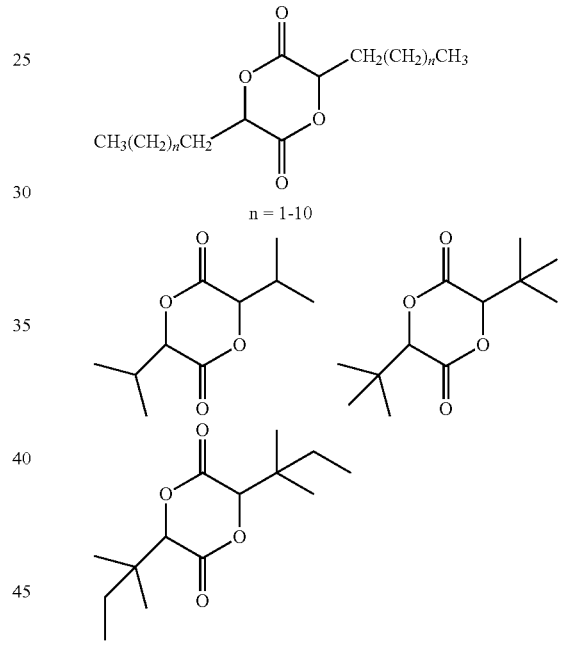

n = 1-10

Diluent Cyclic Ester Monomers

Non-limiting examples of diluent cyclic ester monomers include those of List 3.

List 3

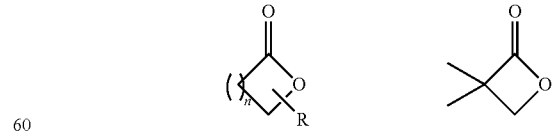

R = H; n = 1: beta-Propiolactone (b-PL)
R = H; n = 2: gamma-Butyrolactone (g-BL)
R = H; n = 3: delta-Valerolactone (d-VL)
R = H; n = 4: epsilon-Caprolactone (e-CL)
R = CH$_3$; n = 1: beta-Butyrolactone (b-BL)
R = CH$_3$; n = 2: gamma-Valerolactone (g-VL)

Pivalolactone (PVL)

-continued

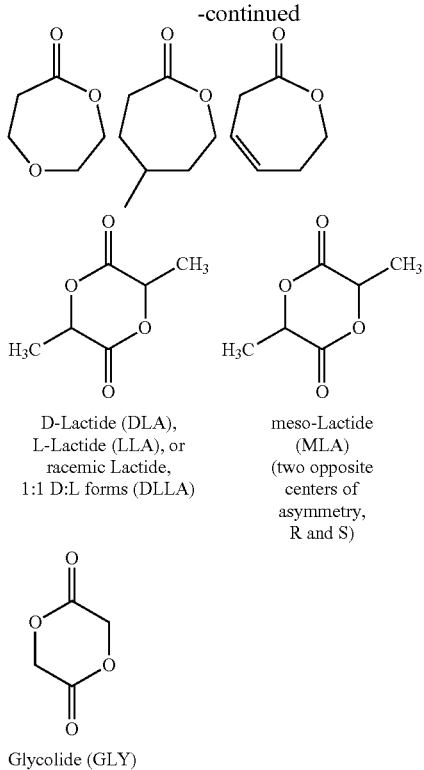

D-Lactide (DLA), L-Lactide (LLA), or racemic Lactide, 1:1 D:L forms (DLLA)

meso-Lactide (MLA) (two opposite centers of asymmetry, R and S)

Glycolide (GLY)

Multi-functional Cyclic Ester Monomers

Non-limiting examples of multi-functional cyclic ester monomers include those of List 4.

List 4

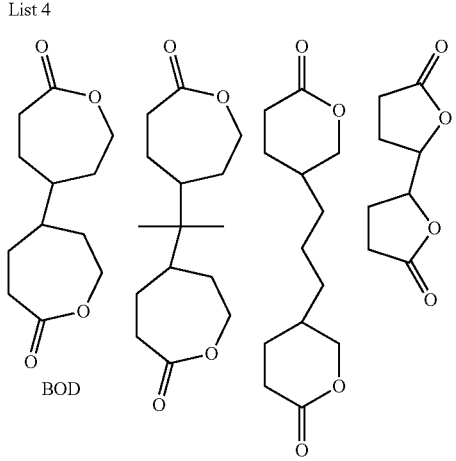

BOD

PEG Initiator

The PEG initiator has a structure according to formula (I-1):

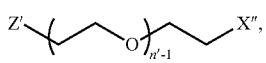

wherein
n' has an average value of about 50 to about 600,
Z' is a monovalent end group,
X" is a nucleophilic monovalent group selected from the group consisting of *—OH, *—$NH_2$, and *—SH, which is capable of initiating a ROP.

Z' can be any suitable end group. Z' can have the same structure as E' of formula (2) or a different structure. Non-limiting exemplary Z' groups include alkyl and aryl oxy groups ($R^eO$—*), alkyl and aryl carboxy groups ($R^eC(=O)O$—*), and alkyl and aryl carboxamido groups ($R^eC(=O)N(H)$—*), wherein $R^e$ is a $C_1$-$C_{10}$ monovalent hydrocarbon radical. In an embodiment, n' has an average value of about 100 to about 200, Z' is methoxy, and X" is *—OH (i.e., the PEG initiator is mono-methyl endcapped poly(ethylene glycol) (MPEG-OH)).

The PEG initiator has one nucleophilic end group selected from the group consisting of alcohols, amines, and thiols. The initiator can have a number average molecular weight (Mn) of about 1000 to about 10000, preferably 1000 to about 5000.

ROP Catalysts

The ROP reaction mixture preferably includes an organocatalyst whose chemical structure contains none of the following restricted metals. An organocatalyst overcomes the problem of entrapped metal, in addition to providing a platform for synthesizing ring opened polymers of controlled, predictable molecular weights and narrow polydispersities.

The term "restricted metals" includes ionic and nonionic forms of beryllium, magnesium, calcium, strontium, barium, radium, aluminum, gallium, indium, thallium, germanium, tin, lead, arsenic, antimony, bismuth, tellurium, polonium, and metals of Groups 3 to 12 of the Periodic Table. Metals of Groups 3 to 12 of the Periodic Table include scandium, titanium, vanadium, chromium, manganese, iron, cobalt, nickel, copper, zinc, yttrium, zirconium, niobium, molybdenum, technetium, ruthenium, rhodium, palladium, silver, cadmium, lanthanum, cerium, praseodymium, neodymium, promethium, samarium, europium, gadolinium, terbium, dysprosium, holmium, erbium, thulium, ytterbium, lutetium, hafnium, tantalum, tungsten, rhenium, osmium, iridium, platinum, gold, mercury, actinium, thorium, protactinium, uranium, neptunium, plutonium, americium, curium, berkelium, californium, einsteinium, fermium, mendelevium, nobelium, lawrencium, rutherfordium, dubnium, seaborgium, bohrium, hassium, meitnerium, darmstadtium, roentgenium, and copernicium.

Preferably, the star polymer formed by the ROP also contains no detectable amount of the above restricted metals. Structural metal from a polymerization catalyst can be entrapped by the crosslinked core. The trapped metal can be cytotoxic and can interfere with the binding, release and/or the function of a cargo material. Therefore, star polymers comprising a minimum of each restricted metal are highly desirable.

No restriction is placed on the concentration of boron, silicon, or any individual alkali metal, with the proviso that the star polymer has desirable loading properties and is suitably non-toxic for its intended use.

The organocatalyst can be an organic acid. Exemplary organic acids include diphenylphosphate, sulfuric acid, p-toluenesulfonic acid, methanesulfonic acid, and trifluoromethane sulfonic acid (triflic acid).

The organocatalyst can be a nitrogen base. The nitrogen base can also serve as an accelerator for another ROP catalyst. Exemplary nitrogen base catalysts include triallylamine, triethylamine, tri-n-octylamine and benzyldimethylamine. Other nitrogen base catalysts, shown in List 5 below, include pyridine (Py), N,N-dimethylaminocyclohexane (Me₂NCy), 4-N,N-dimethylaminopyridine (DMAP), trans-1,2-bis(dimethylamino)cyclohexane (TMCHD), 1,8-diazabicyclo[5.4.0]undec-7-ene (DBU), 1,5,7-triazabicyclo[4.4.0]dec-5-ene (TBD), 7-methyl-1,5,7-triazabicyclo[4.4.0]dec-5-ene (MTBD), (-)-sparteine, (Sp) 1,3-bis(2-propyl)-4,5-dimethylimidazol-2-ylidene (Im-1), 1,3-bis(2,4,6-trimethylphenyl)imidazol-2-ylidene (Im-2), 1,3-bis(2,6-di-i-propylphenyl(imidazol-2-ylidene (Im-3), 1,3-bis(1-adamantyl)imidazol-2-ylidene (Im-4), 1,3-di-i-propylimidazol-2-ylidene (Im-5), 1,3-di-t-butylimidazol-2-ylidene (Im-6), 1,3-bis(2,4,6-trimethylphenyl)-4,5-dihydroimidazol-2-ylidene (Im-7), 1,3-bis(2,6-di-i-propylphenyl)-4,5-dihydroimidazol-2-ylidene, 1,3-bis(2,6-di-i-propylphenyl)-4,5-dihydroimidazol-2-ylidene (Im-8) or a combination thereof.

List 5

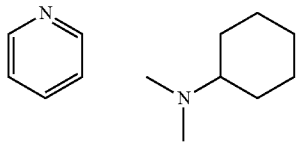

Pyridine (Py)    N,N-Dimethylaminocyclohexane (Me2NCy)

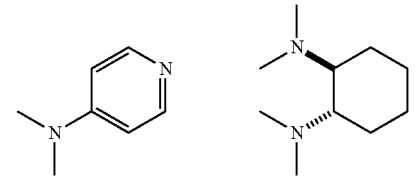

4-N,N-Dimethylaminopyridine (DMAP)    trans 1,2-Bis(dimethylamino)-cyclohexane (TMCHD)

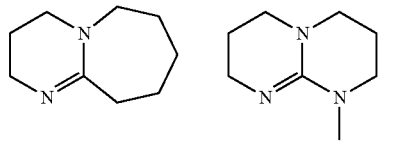

1,8-Diazabicyclo[5.4.0]-undec-7-ene (DBU)    7-Methyl-1,5,7-triazabicyclo-[4.4.0]dec-5-ene (MTBD)

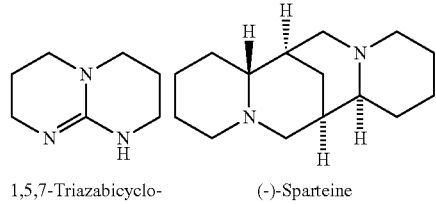

1,5,7-Triazabicyclo-[4.4.0]dec-5-ene (TBD)    (-)-Sparteine (Sp)

(Im-1)

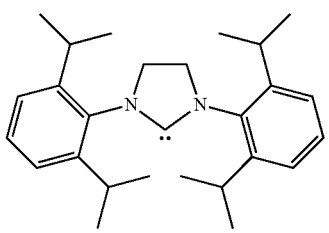

1,3-Bis(2-propyl)-4,5-dimethylimidazol-2-ylidene (Im-2)

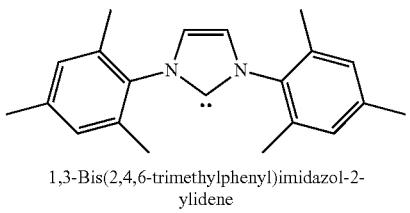

1,3-Bis(2,4,6-trimethylphenyl)imidazol-2-ylidene (Im-3)

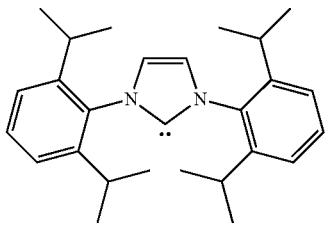

1,3-Bis(2,6-di-i-propylphenyl(imidazol-2-ylidene (Im-4)

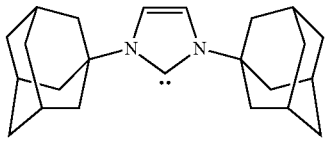

1,3-Bis(1-adamantyl)imidazol-2-yliden)

(Im-5)

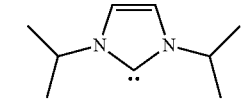

1,3-Di-i-propylimidazol-2-ylidene (Im-6)

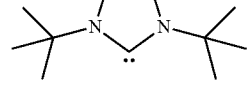

1,3-Di-t-butylimidazol-2-ylidene (Im-7)

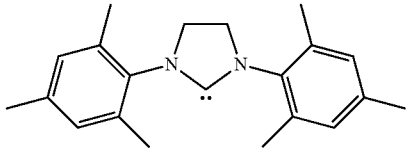

1,3-Bis(2,4,6-trimethylphenyl)-4,5-dihydroimidazol-2-ylidene (Im-8)

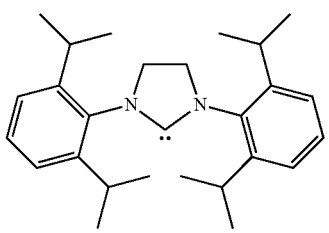

1,3-Bis(2,6-di-i-propylphenyl)-4,5-dihydroimidazol-2-ylidene

A more specific organocatalyst is N-bis(3,5-trifluoromethyl)phenyl-N'-cyclohexylthiourea (TU):

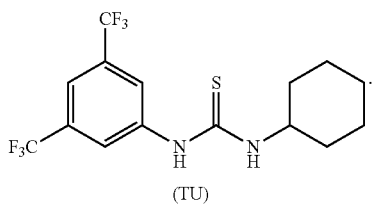

(TU)

Other organocatalysts comprise at least one 1,1,1,3,3,3-hexafluoropropan-2-ol-2-yl (HFP) group. Singly-donating hydrogen bond catalysts have the formula (C-1):

$$R^2\text{—}C(CF_3)_2OH \quad (C\text{-}1),$$

wherein $R^2$ represents a hydrogen (H—*) or a monovalent group having 1 to 20 carbons, for example an alkyl group, substituted alkyl group, cycloalkyl group, substituted cycloalkyl group, heterocycloalkyl group, substituted heterocycloalklyl group, aryl group, substituted aryl group, or a combination thereof. Exemplary singly-donating hydrogen bonding catalysts are shown in List 6.

List 6

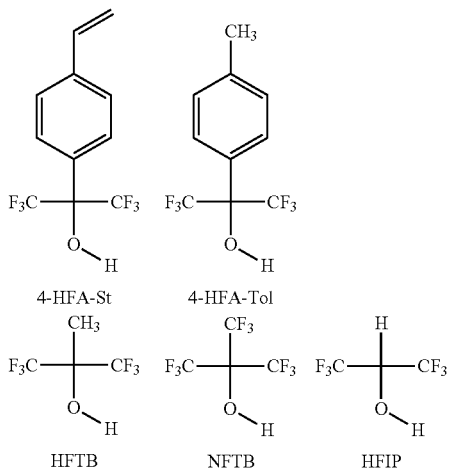

Other ROP organocatalysts include doubly-donating hydrogen bonding catalysts having two HFP groups, represented by the formula (C-2):

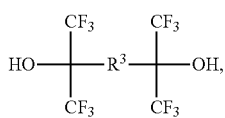

wherein $R^3$ is a divalent radical bridging group comprising 1 to 20 carbons, such as an alkylene group, a substituted alkylene group, a cycloalkylene group, substituted cycloalkylene group, a heterocycloalkylene group, substituted heterocycloalkylene group, an arylene group, a substituted arylene group, or a combination thereof. Representative double hydrogen bonding catalysts of formula (C-2) include those of List 7 below. In a specific embodiment, $R^3$ is an arylene or substituted arylene group, and the HFP groups occupy positions meta to each other on the aromatic ring.

List 7

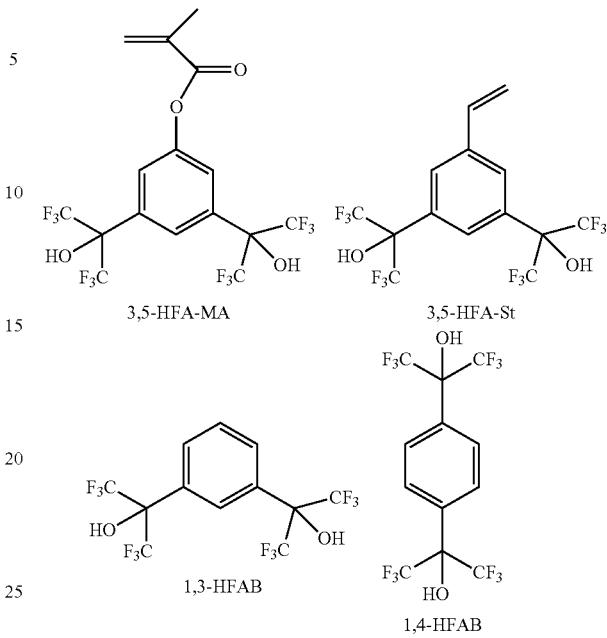

In one embodiment, the catalyst is selected from the group consisting of 4-HFA-St, 4-HFA-Tol, HFTB, NFTB, HPIP, 3,5-HFA-MA, 3,5-HFA-St, 1,3-HFAB, 1,4-HFAB, and combinations thereof.

The HFP-containing groups can be covalently bound to a support. In one embodiment, the support comprises a polymer, a crosslinked polymer bead, an inorganic particle, or a metallic particle. HFP-containing polymers can be formed by known methods including direct polymerization of an HFP-containing monomer (for example, the methacrylate monomer 3,5-HFA-MA or the styryl monomer 3,5-HFA-St). Functional groups in HFP-containing monomers that can undergo direct polymerization (or polymerization with a comonomer) include acrylate, methacrylate, alpha, alpha, alpha-trifluoromethacrylate, alpha-halomethacrylate, acrylamido, methacrylamido, norbornene, vinyl, vinyl ether, and other groups known in the art. Examples of linking groups include $C_1$-$C_{12}$ alkyl, a $C_1$-$C_{12}$ heteroalkyl, ether group, thioether group, amino group, ester group, amide group, or a combination thereof.

The catalyst comprising charged HFP-containing groups can be bound by ionic association to oppositely charged sites on a polymer or a support surface.

The nitrogen base can be used alone as a catalyst when producing linear polymers by ring opening polymerization, such as the polymer arm precursor. Alternatively, the nitrogen bases can serve as an optional accelerator when used in combination with a primary catalyst, such as TU, in a ring opening polymerization. When employed as an accelerator, each nitrogen is potentially capable of participating as a Lewis base. In general, stronger nitrogen base accelerators improve the polymerization rate.

The ROP reaction mixture comprises at least one organocatalyst and, when appropriate, several organocatalysts together. The ROP catalyst can be added in a proportion of 1/20 to 1/40,000 moles relative to the cyclic carbonyl monomers, and preferably in a proportion of 1/1,000 to 1/20,000 moles relative to the cyclic carbonyl monomers.

Exceptions to the above have been found when attempting to generate the crosslinked core by ring opening polymerization using base catalysis alone. In these instances, nitrogen bases comprising 1 or 2 nitrogens have not generally been effective in forming unimolecular star polymers. The 1-nitrogen and 2-nitrogen base catalysts produced star polymers having high polydispersities (greater than 1.35), or products that were amorphous. After considerable experimentation, it was found that the formation of the crosslinked core by ring opening polymerization of a multi-functional cyclic ester monomer could be accomplished using a nitrogen base comprising three or more nitrogens. Unimolecular nano-sized amphiphilic star polymers having a polydispersity of 1.35 or less were successfully produced using this type of catalyst. One such base catalyst is 1,5,7-triazabicyclo[4.4.0]dec-5-ene (TBD). The examples further below demonstrate formation of a star polymer using TBD as the sole catalyst.

ROP Conditions

The ring-opening polymerization can be performed at a temperature of about 15° C. to 150° C., more preferably 20° C. to 80° C. Reaction times vary with solvent, temperature, agitation rate, pressure, and equipment. In general, the polymerizations are complete within 1 to 100 hours.

The ROP reaction is preferably performed with a solvent. Exemplary solvents include dichloromethane, chloroform, benzene, toluene, xylene, chlorobenzene, dichlorobenzene, benzotrifluoride, petroleum ether, acetonitrile, pentane, hexane, heptane, 2,2,4-trimethylpentane, cyclohexane, diethyl ether, t-butyl methyl ether, diisopropyl ether, dioxane, tetrahydrofuran, or a combination comprising one of the foregoing solvents. A suitable monomer concentration is about 0.1 to 5 moles per liter, and more particularly about 0.2 to 4 moles per liter.

The ROP polymerizations are conducted using a dry, inert atmosphere, such as nitrogen or argon, and at a pressure of 100 MPa to 500 MPa (1 atm to 5 atm), more typically at a pressure of 100 MPa to 200 MPa (1 atm to 2 atm). At the completion of the reaction, the solvent can be removed using reduced pressure.

The catalyst and the accelerator can be the same material. For example, some ring opening polymerizations can be conducted using 1,5,7-triazabicyclo[4.4.0]dec-5-ene (TBD) alone, with no another catalyst or accelerator present.

The catalyst is preferably present in an amount of about 0.2 to 20 mol %, 0.5 to 10 mol %, 1 to 5 mol %, or 1 to 2.5 mol %, based on total moles of cyclic carbonyl monomer(s) used.

The nitrogen base accelerator, when used, is preferably present in an amount of 0.1 to 5.0 mol %, 0.1 to 2.5 mol %, 0.1 to 1.0 mol %, or 0.2 to 0.5 mol %, based on total moles of cyclic ester monomer used for the ROP.

The initiator groups are preferably present in an amount of 0.001 to 10.0 mol %, 0.1 to 2.5 mol %, 0.1 to 1.0 mol %, and 0.2 to 0.5 mol %, based on total moles of cyclic carbonyl monomer(s).

The catalysts can be removed by selective precipitation or in the case of the solid supported catalysts, simply by filtration. The radical polymer can comprise residual catalyst in an amount greater than or equal to 0 wt % (weight percent), based on total weight of the radical polymer and the residual catalyst.

Average Molecular Weight

The polyester block P''' preferably has a number average molecular weight Mn of about 1000 or more, more preferably about 1000 to about 50,000, and most preferably about 1000 to about 20,000. In an embodiment, the polyester block P''' has a number average molecular weight Mn of about 3000 to about 10,000.

The polyester block P''' can have a polydispersity index (PDI) of 1.01 to 2.0, more preferably 1.01 to 1.30, and even more preferably 1.01 to 1.25.

The core preferably has a number average molecular weight Mn of about 10,000 or more, more preferably about 20,000 to about 40,000, and most preferably about 25,000 to about 35,000.

Endcap Agents

Optionally, the crosslinked core can further be treated with an endcap agent to prevent further chain growth and stabilize the reactive end groups against unwanted side reactions such as chain scission. Endcap agents include, for example, materials for converting terminal hydroxyl groups to esters, such as carboxylic acid anhydrides and carboxylic acid chlorides. The endcap agent can also comprise a biologically active moiety, which becomes bound to the terminal end group of the ring opened polymer chain.

In an embodiment, the core comprises a living end group (i.e., is not endcapped), and is capable of initiating a ring opening polymerization. In aqueous solution the star polymers disperse to form nano-sized particles having an average particle size of from 2 nm to 500 nm, 10 nm to 250 nm, and more particularly 50 nm to 200 nm, 50 nm to 150 nm, 50 nm to 120 nm, and even more particularly from 50 nm to 100 nm, as measured by dynamic light scattering. The particles can comprise one or more macromolecules of the star polymer.

Loaded Star Polymers

Figure 2:
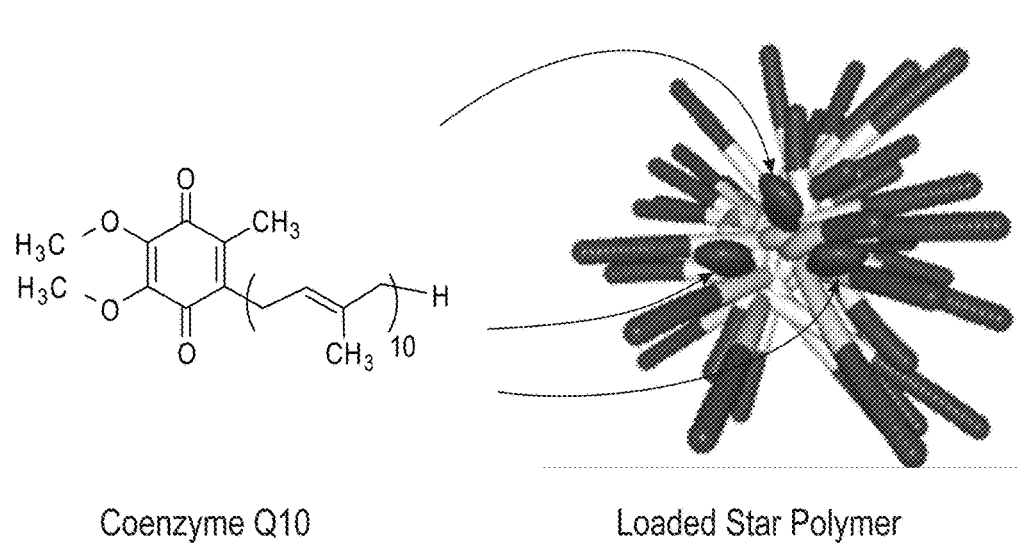
FIG. 2 is an illustration showing an exemplary non-limiting loaded star polymer, where 3 molecules of cargo, CoQ10, are occluded within the hydrophobic region of the star polymer arms.

FIG. 2 is an illustration showing an exemplary non-limiting loaded star polymer, where 3 molecules of cargo, Coenzyme Q10 (CoQ10), are occluded within the hydrophobic region of the star polymer arms. In this example, the cargo and the star polymer are bound by non-covalent interactions.

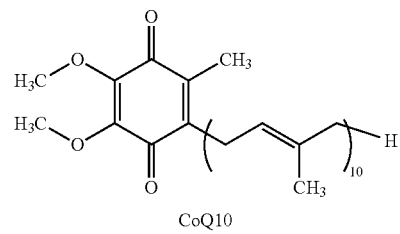

CoQ10

No limitation is placed on the cargo material, with the proviso that the loaded star polymer can be dispersed in aqueous solution in the form of nano-sized particles, and the loaded star polymer comprising the cargo performs a useful function. Cargo materials include biologically active substances. Exemplary biologically active substances include biomolecules (e.g., DNA, genes, peptides, proteins, enzymes, lipids, phospholipids, and nucleotides), natural or synthetic organic compounds (e.g., drugs, dyes, synthetic polymers, oligomers, and amino acids), vitamins (e.g., vitamin E compounds, vitamin D), dietary supplements (e.g., coenzyme Q10 (CoQ10, ubiquinone), ubiquinol), inorganic materials (e.g., metals and metal oxides), chromophores that aid in diagnostics (e.g., porphyrinoid compounds, including porphyrins and phthalocyanines), radioactive variants of the foregoing, and combinations of the foregoing. Some of the biologically active substances can alter the chemical structure and/or activity of a cell, or can selectively alter the chemical structure and/or activity of a cell type relative to another cell type. As an example, one desirable change in a chemical structure can be the incorporation of a gene into the DNA of the cell. A desirable change in activity can be the expression of the transfected gene. Another change in cell activity can be the induced production of a desired hormone or enzyme. A desirable change in cell activity can also be the selective death of one cell type over another cell type. No limitation is placed on the relative change in cellular activity caused by the biologically active substance, providing the change is desirable and useful. Other biologically active materials herein improve diagnostic capability without necessarily altering the structure or activity of the tissue, organ, bone, or cell. These include image contrast enhancing agents for magnetic resonance imaging and x-ray imaging. The cargo material can comprise a metal, including one or more of the above-described restricted metals.

The cargo material can be bound covalently or non-covalently (e.g., by hydrophobic, hydrogen bonding, and/or electrostatic interactions) to the star polymer. The cargo material does not have to be released from the loaded star polymer in order to perform a useful function. The cargo material can perform a useful function while bound to the star polymer or after release from the star polymer.

The loaded star polymer can be administered as a powder, pill, paste, lotion, gel, or aqueous mixture using any suitable technique, including but not limited to liquid injections, solid or liquid ingestion, vapor inhalers, spray-on liquids, topically applied lotions, transdermal patches, solid and gel suppositories, ophthalmic gels, and/or ophthalmic drops.

In aqueous solution at a pH of from 5.0 to 8.0, the loaded star polymers are nano-sized particles, which can have an average cross-sectional circular diameter of from 2 nm to 500 nm, 2 nm to 250 nm, 2 nm to 150 nm, 2 nm to 120 nm, and more particularly 10 nm to 120 nm, 20 nm to 120 nm, 30 nm to 120 nm, and even more particularly from 50 nm to 120 nm, as measured by dynamic light scattering. A loaded star polymer can comprise, for example 0.1 to 90 wt. %, more particularly 5 to 50 wt %, and even more particularly 15 to 50 wt % of a biologically active material based on total dry weight of the loaded star polymer.

The loaded star polymers can comprise both small molecular weight biologically active materials having a molecular weight in a range from 100 daltons to about 1,000 daltons as well as larger macromolecular materials, such as peptide and protein drugs having a molecular weight in a range from about 1,000 daltons to about 100,000 daltons, and beyond.

Contrast enhancing agents that have been considered for nuclear magnetic resonance imaging include soluble salts of paramagnetic metal ions, paramagnetic chelates and metallic complexes, and nitroxide stable free radicals. Paramagnetic metals ions include: from the transition metals series: titanium ($Ti^{3+}$), iron ($Fe^{3+}$), vanadium ($V^{4+}$), cobalt ($Co^{3+}$), chromium ($Cr^{3+}$), nickel ($Ni^{2+}$), manganese ($Mn^{2+}$), and copper ($Cu^{2+}$); from the Lanthanide series: praseodynium ($Pr^{3+}$), gadolinium ($Gd^{3+}$), europium ($Eu^{3+}$), and dysprosium ($Dy^{3+}$); from the Actinide series: protactinium ($Pa^{4+}$); and from nitroxide stable free radicals: pyrrolidine derivatives, and piperidine derivatives. Of these, the most favored contrast enhancing agents include complexes of ferric, chromium, and gadolinium ions, and stable nitroxide free radicals. Exemplary contrast enhancing agents for x-ray imaging include barium salts and halogenated materials, more particularly brominated and/or iodinated materials.

Organic contrast enhancing agents include porphyrinoids, which include but are not limited to porphyrins, corrins, chlorins, bacteriochlorophylls, phthalocyanines, tetraazaphyrins, texaphyrins, saphyrins, and the like. A nonlimiting example of a porphyrinoid compound is 5,10,15,20-(3,5-ditertbutylphenyl)porphyrin, where the ligand M can be a metal or two hydrogens (M=2H) (DTBP):

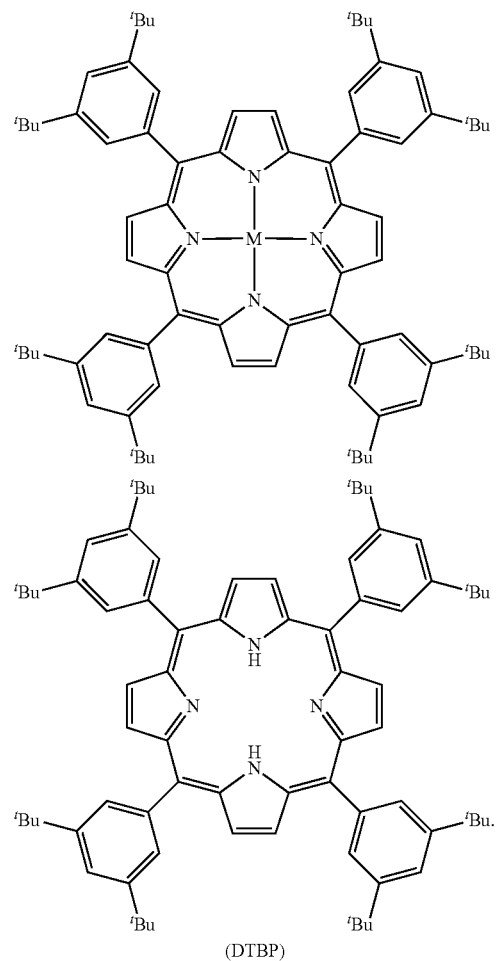

(DTBP)

Another nonlimiting example of a porphyrinoid compound is tert-butyl phthalocyanine, wherein the ligand M can be a metal or two hydrogens (M=2H) (TBP):

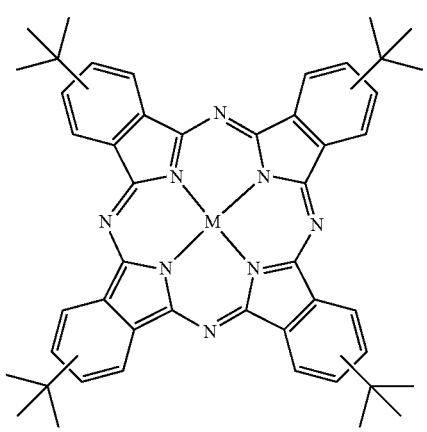

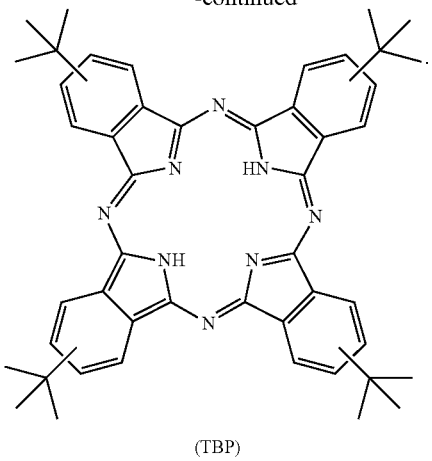

(TBP)

The contrast enhancing material can also comprise a combination of a porphyrinoid compounds. The porphyrinoid compound can further comprise a metal ligand that is a restricted metal.

The porphyrinoid compound can be in a non-aggregated state in the loaded star polymer, detectable by the fluorescence of an aqueous mixture of the loaded star polymer. In an embodiment, 10% to 100% by weight of the porphyrinoid compound in the loaded star polymer is in a non-aggregated state. In another embodiment, 50% to 100% by weight of the porphyrinoid compound in the loaded star polymer is in a non-aggregated state.

Exemplary protein drugs include peptide hormones such as insulin, glucagon, parathyroid hormone, calcitonin, vasopression, renin, prolactin, growth hormone, the gonadotropins including chorionic gonadotropin, follicle stimulating hormone, thyroid stimulating hormone and leutenizing hormone; physiologically active enzymes such as transferases, hydrolases, lyases, isomerases, phosphatases, glycosidases, superoxide dismutase, factor VIII, plasminogen activators; and other therapeutic agents including protein factors such as epidermal growth factor, insulin-like growth factor, tumour necrosis factor, transforming growth factors, fibroblast growth factors, patelet-derived growth factors, erythropoietin, colony stimulating factors, bone morphogenetic proteins, interleukins and interferons. Exemplary non-protein macromolecules include polysaccharides, nucleic acid polymers, and therapeutic secondary metabolites including plant products such as vinblastine, vincristine, taxol and the like.

Other non-limiting commercially available drugs include the following, where the generic drug is enclosed in parentheses: 13-cis-Retinoic Acid, 2-CdA (Cladribine), 2-Chlorodeoxyadenosine (Cladribine), 5-Azacitidine, 5-Fluorouracil (Fluorouracil), 5-FU (Fluorouracil), 6-Mercaptopurine, 6-MP (6-Mercaptopurine), 6-TG (Thioguanine), 6-Thioguanine (Thioguanine), ABRAXANE® (Paclitaxel protein bound), ACCUTANE® (Isotretinoin), Actinomycin-D (Dactinomycin), ADRIAMYCIN® (Doxorubicin), ADRUCIL® (Fluorouracil), AFINITOR® (Everolimus), AGRYLIN® (Anagrelide), ALA-CORT® (Hydrocortisone), Aldesleukin, Alemtuzumab, ALIMTA® (Pemetrexed), Alitretinoin (9-cis-retinoic acid), Alkaban-AQ (Vinblastine), ALKERAN® (Melphalan), All-transretinoic Acid (Tretinoin), Alpha Interferon (Interferon Alfa), Altretamine, Amethopterin (Methotrexate), Amifostine, Aminoglutethimide, Anagrelide, ANANDRON® (Nilutamide), Anastrozole, Arabinosylcytosine (Cytarabine), Ara-C(Cytarabine), ARANESP® (Darbepoetin Alfa), AREDIA® (Pamidronate), ARIMIDEX® (Anastrozole), AROMASIN® (Exemestane), ARRANON® (Nelarabine), Arsenic Trioxide, Asparaginase, ATRA (All-transretinoic Acid), AVASTIN® (Bevacizumab), Azacitidine, BCG, BCNU (Carmustine), Bendamustine (Bendamustine Hydrochloride), Bevacizumab, Bexarotene, BEXXAR® (Tositumomab), Bicalutamide, BICNU® (Carmustine), BLENOXANE® (Bleomycin), Bleomycin, Bortezomib, Busulfan, BUSULFEX® (Busulfan), C225 (Cetuximab), Calcium Leucovorin (Leucovorin), CAMPATH® (Alemtuzumab), CAMPTOSAR® (Irinotecan), Camptothecin-11 (Irinotecan), Capecitabine, CARAC® (Fluorouracil), Carboplatin, Carmustine, Carmustine Wafer, CASODEX® (Bicalutamide), CC-5013 (Lenalidomide), CCI-779 (Temsirolimus), CCNU (Lomustine), CDDP (Cisplatin), CEENU® (Lomustine), CERUBIDINE® (Daunomycin), Cetuximab, Chlorambucil, Cisplatin, Citrovorum Factor (Leucovorin), Cladribine, Cortisone (Hydrocortisone), COSMOGEN® (Dactinomycin), CPT-11 (Irinotecan), Cyclophosphamide, CYTADREN® (Aminoglutethimide), Cytarabine, Cytarabine Liposomal, CYTOSAR-U® (Cytarabine), CYTOXAN® (Cyclophosphamide), Dacarbazine, DACOGEN® (Decitabine), Dactinomycin, Darbepoetin Alfa, Dasatinib, Daunomycin, Daunorubicin, Daunorubicin Hydrochloride, Daunorubicin Liposomal, DAUNOXOME® (Daunorubicin Liposomal), DECADRON™ (Dexamethasone), Decitabine, DELTA-CORTEF® (Prednisolone), DELTASONE® (Prednisone), Denileukin Diftitox, DEPOCYT® (Cytarabine Liposomal), Dexamethasone, Dexamethasone Acetate, Dexamethasone Sodium Phosphate, DEXASONE® (Dexamethasone), Dexrazoxane, DHAD (Mitoxantrone), DIC (Dacarbazine), DIODEX® (Dexamethasone), Docetaxel, DOXIL® (Doxorubicin Liposomal), Doxorubicin, Doxorubicin Liposomal, DROXIA® (Hydroxyurea), DTIC (Dacarbazine), DTIC-DOME® (Decarbazine), Duralone (Methylprednisolone), EFUDEX® (Fluorouracil), ELIGARD® (Leuprolide), ELLENCE® (Epirubicin), ELOXATIN® (Oxaliplatin), ELSPAR® (Asparaginase), EMCYT® (Estramustine), Epirubicin, Epoetin Alfa, ERBITUX® (Cetuximab), Erlotinib, Erwinia L-asparaginase (Asparaginase), Estramustine, ETHYOL® (Amifostine), ETOPOPHOS® (Etoposide), Etoposide, Etoposide Phosphate, EULEXIN® (Flutamide), Everolimus, EVISTA® (Raloxifene), Exemestane, FARESTON® (Toremifene), FASLODEX® (Fulvestrant), FEMARA® (Letrozole), Filgrastim, Floxuridine, FLUDARA® (Fludarabine), Fludarabine, FLUOROPLE® (Fluorouracil), Fluorouracil, Fluorouracil (cream), Fluoxymesterone, Flutamide, Folinic Acid (Leucovorin), FUDR® (Floxuridine), Fulvestrant, G-CSF (Pegfilgrastim), Gefitinib, Gemcitabine, Gemtuzumab ozogamicin, GEMZAR® (Gemcitabine), GLEEVEC® (Imatinib mesylate), GLIADEL® Wafer (Carmustine Wafer), GM-CSF (Sargramostim), Goserelin, Granulocyte—Colony Stimulating Factor (Pegfilgrastim), Granulocyte Macrophage Colony Stimulating Factor (Sargramostim), HALOTESTIN® (Fluoxymesterone), HERCEPTIN® (Trastuzumab), HEXADROL® (Dexamethasone), HEXALEN® (Altretamine), Hexamethylmelamine (Altretamine), HMM (Altretamine), HYCAMTIN® (Topotecan), HYDREA® (Hydroxyurea), Hydrocort Acetate (Hydrocortisone), Hydrocortisone, Hydrocortisone Sodium Phosphate, Hydrocortisone Sodium Succinate, HYDROCORTONE® Phosphate (Hydrocortisone), Hydroxyurea, Ibritumomab, Ibritumomab Tiuxetan (Ibritumomab), IDAMYCIN® (Idarubicin), Idarubicin, IFEX® (Ifosfamide), IFN-alpha (Interferon alfa), Ifosfamide, IL-11 (Oprelvekin), IL-2 (Aldesleukin), Imatinib mesylate, Imidazole Carboxamide (Decarbazine), Interferon alfa, Interferon Alfa-2b (PEG Conjugate), Interleukin-2 (Aldesleukin), Interleukin-11 (Oprelvekin), INTRON® A (interferon alfa-2b), IRESSA® (Gefitinib), Irinotecan, Isotretinoin, Ixabepilone, IXEMPRA® (Ixabepilone), Kidrolase (Asparaginase), LANACORT® (Hydrocortisone), Lapatinib, L-asparaginase, LCR (Vincristine), Lenalidomide, Letrozole, Leucovorin, LEUKERAN® (Chlorambucil), LEUKINE® (Sargramostim), Leuprolide, Leurocristine (Vincristine), LEUSTATIN® (Cladribine), Liposomal Ara-C, LIQUID PRED® (Prednisone), Lomustine, L-PAM (Melphalen), L-Sarcolysin (Melphalen), LUPRON® (Leuprolide), LUPRON DEPOT® (Leuprolide), MATULANE® (Procarbazine), MAXIDEX® (Dexamethasone), Mechlorethamine, Mechlorethamine Hydrochloride, Medralone (Methylprednisolone), MEDROL® (Methylprednisolone), MEGACE® (Megestrol), Megestrol, Megestrol Acetate (Megastrol), Melphalan, Mercaptopurine (6-Mercaptopurine), Mesna, MESNEX® (Mesna), Methotrexate, Methotrexate Sodium (Methotrexate), Methylprednisolone, METICORTEN® (Prednisone), Mitomycin (Mitomycin C), Mitomycin-C, Mitoxantrone, M-Prednisol (Methylprednisolone), MTC (Mitomycin-C), MTX (Methotrexate), MUSTARGEN® (Mechlorethamine), Mustine (Mechlorethamine), MUTAMYCIN® (Mitomycin-C), MYLERAN® (Busulfan), MYLOCEL® (Hydroxyurea), MYLOTARG® (Gemtuzumab ozogamicin), NAVELBINE® (Vinorelbine), Nelarabine, NEOSAR® (Cyclophosphamide), NEULASTA® (Pegfilgrastim), NEUMEGA® (Oprelvekin), NEUPOGEN® (Filgrastim), NEXAVAR® (Sorafenib), NILANDRON® (Nilutamide), Nilutamide, NIPENT® (Pentostatin), Nitrogen Mustard (Mechlorethamine), NOLVADEX® (Tamoxifen), NOVANTRONE® (Mitoxantrone), Octreotide, Octreotide acetate (Octreotide), ONCASPAR® (Pegaspargase), ONCOVIN® (Vincristine), ONTAK® (Denileukin Diftitox), ONXOL® (Paclitaxel), Oprelvekin (Interleukin-11), ORAPRED® (Prednisolone), ORASONE® (Prednisone), Oxaliplatin, Paclitaxel, Paclitaxel Protein-bound, Pamidronate, Panitumumab, PANRETIN® (Alitretinoin), PARAPLATIN® (Carboplatin), PEDIAPRED® (Prednisolone), PEG Interferon, Pegaspargase, Pegfilgrastim, PEG-INTRON® (Interferon Alfa-2b), PEG-L-asparaginase, Pemetrexed, Pentostatin, Phenylalanine Mustard (Melphalen), PLATINOL® (Cisplatin), Platinol-AQ (Cisplatin), Prednisolone, Prednisone, PRELONE® (Prednisolone), Procarbazine, PROCRIT® (Epoetin Alfa), PROLEUKIN® (Aldesleukin), Prolifeprospan 20 with Carmustine Implant (Carmustine Wafer), PURINETHOL® (6-Mercaptopurine), Raloxifene, REVLIMID® (Lenalidomide), RHEUMATREX® (Methotrexate), RITUXAN® (Rituximab), Rituximab, Roferon-A (Interferon Alfa-2a), RUBEX® (Doxorubicin), Rubidomycin hydrochloride (Daunomycin), SANDOSTATIN® (Octreotide), SANDOSTATIN LAR® (Octreotide), Sargramostim, SOLU-CORTEF® (Hydrocortisone), SOLU-MEDROL® (Methylprednisolone), Sorafenib, SPRYCEL® (Dasatinib), STI-571 (Imatinib Mesylate), Streptozocin, SU11248 (Sunitinib), Sunitinib, SUTENT® (Sunitinib), Tamoxifen, TARCEVA® (Erlotinib), TARGRETIN® (Bexarotene), TAXOL® (Paclitaxel), TAXOTERE® (Docetaxel), TEMODAR® (Temozolomide), Temozolomide, Temsirolimus, Teniposide, TESPA (Thiotepa), Thalidomide, THALOMID® (Thalidomide), THERACYS® (BCG), Thioguanine, Thioguanine Tabloid (Thioguanine), Thiophosphoamide (Thiotepa), THIOPLEX® (Thiotepa), Thiotepa, TICE® (BCG), TOPOSAR® (Etoposide), Topotecan, Toremifene, TORISEL® (Temsirolimus), Tositumomab, Trastuzumab, TREANDA® (Bendamustine Hydrochloride), Tretinoin, TREXALL® (Methotrexate), TRISENOX® (Arsenic Trioxide), TSPA (Thiotepa), TYKERB® (Lapatinib), VCR (Vincristine), VECTIBIX® (Panitumumab), VELBAN® (Vinblastine), VELCADE® (Bortezomib), VEPESID® (Etoposide), VESANOID® (Tretinoin), VIADUR® (Leuprolide), VIDAZA® (Azacitidine), Vinblastine, Vinblastine Sulfate, VINCASAR PFS® (Vincristine), Vincristine, Vinorelbine, Vinorelbine tartrate (Vinorelbine), VLB (Vinblastine), VM-26 (Teniposide), Vorinostat, VP-16 (Etoposide), VUMON® (Teniposide), XELODA® (Capecitabine), ZANOSAR® (Streptozocin), ZEVALIN® (Ibritumomab), ZINECARD® (Dexrazoxane), ZOLADEX® (Goserelin), Zoledronic acid, ZOLINZA® (Vorinostat), and ZOMETA® (Zoledronic acid).

In an embodiment, the cargo is selected from the group consisting of CoQ10, ubiquinol, and combinations thereof.

Also disclosed is a method of preparing a loaded star polymer, comprising i) forming a mixture of an amphiphilic star polymer and a biologically active material in a first solvent; and ii) injecting the mixture into a second solvent, the second solvent being a non-solvent for the biologically active material, thereby forming nanoparticles of a loaded star polymer; wherein the star polymer comprises a crosslinked microgel core and 6 or more independent polymer arms covalently linked to the core, the 6 or more polymer arms each comprise a hydrophobic chain segment and a hydrophilic chain segment, and the star polymer comprises no more than 100 ppm of any single restricted metal.

Also disclosed is an aqueous mixture comprising i) a star polymer comprising a crosslinked living microgel core and 6 or more independent polymer arms covalently linked to the core, the 6 or more arms each comprising a hydrophilic polymer chain segment and a hydrophobic polymer chain segment, the star polymer comprising no more than 100 ppm of any single restricted metal; and ii) a biologically active material in contact with the microgel core and/or with the 6 or more independent polymer arms. In an embodiment the biologically active material is an image contrast enhancing material. In another embodiment, the contrast enhancing material is a porphyrinoid compound. In another embodiment, the biologically active material is selected from the group consisting of CoQ10, ubiquinol, and combinations thereof. In another embodiment, the contrast enhancing material is selected from the group consisting of

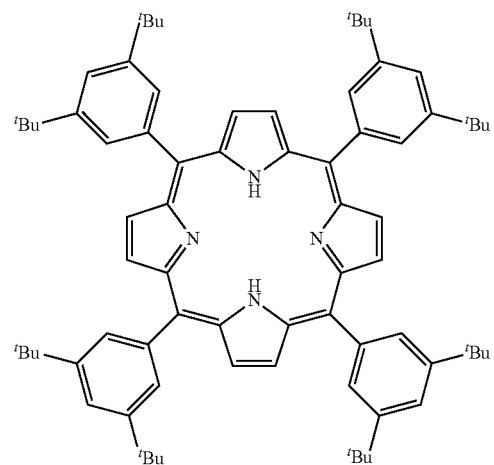

-continued

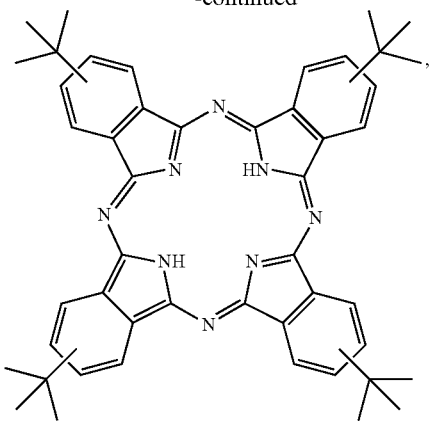

and combinations thereof.

In another embodiment, 10% to 100% of the image enhancing material is not aggregated in the loaded star polymer. In another embodiment, 50% to 100% of the image enhancing material is not aggregated in the loaded star polymer.

Further disclosed is a method of treating a cell, comprising contacting the cell with an aqueous mixture comprising the above described loaded star polymer. The biologically active cargo can comprise a single biologically active material or a mixture of biologically active materials. The biologically active material can be a substance selected from the group consisting of drugs, genes, dyes, image contrast enhancing materials, and combinations thereof. The biologically active cargo can be a drug, for example doxorubicin. In an embodiment, the biologically active material is a porphyrinoid compound. Cells can be contacted in vitro, ex vivo, or in vivo. Contacting induces 0% to 20%, 0% to 15%, 0% to 10%, 0% to 5%, 0% to 2%, or more particularly 0% to 1% cytotoxicity. In an embodiment, contacting induces no cytotoxicity.

No restriction is placed on the type of cell that can be treated with the above-described loaded nanoparticles. In particular, the cells can be eukaryotic cells, mammalian cells, and more particularly rodent or human cells. The cells can be derived from various tissues, including extraembryonic or embryonic stem cells, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, dendritic cells, neurons, glia, mast cells, blood cells and leukocytes (e.g., erythrocytes, megakaryotes, lymphocytes, such as B, T and natural killer cells, macrophages, neutrophils, eosinophils, basophils, platelets, granulocytes), epithelial cells, keratinocytes, chondrocytes, osteoblasts, osteoclasts, hepatocytes, and cells of the endocrine or exocrine glands, as well as sensory cells.

The above-described loaded star polymers can be used as non-viral transfection vectors. The target gene is not limited to any particular type of target gene or nucleotide sequence. For example, the target gene can be a cellular gene, an endogenous gene, an oncogene, a transgene, or a viral gene including translated and non-translated RNAs. Exemplary possible target genes include: transcription factors and developmental genes (e.g., adhesion molecules, cyclin-dependent kinase inhibitors, Wnt family members, Pax family members, Winged helix family members, Hox family members, cytokines/lymphokines and their receptors, growth/differentiation factors and their receptors, neurotransmitters and their receptors); oncogenes (e.g., ABLI, BCLI, BCL2, BCL6, CBFA2, CBL, CSFIR, ERBA, ERBB, ERBB2, ETSI, ETV6, FGR, FOS, FYN, HCR, HRAS, JUN, KRAS, LCK, LYN, MDM2, MLL, MYB, MYC, MYCLI, MYCN, NRAS, PIMI, PML, RET, SKP2, SRC, TALI, TCL3, and YES); tumor suppressor genes (e.g., APC, BRAI, BRCA2, CTMP, MADH4, MCC, NFI, NF2, RBI, TP53, and WTI); and enzymes (e.g., ACP desaturases and hydroxylases, ADP-glucose pyrophorylases, ATPases, alcohol dehydrogenases, amylases, amyloglucosidases, catalases, cyclooxygenases, decarboxylases, dextrinases, DNA and RNA polymerases, galactosidases, glucose oxidases, GTPases, helicases, integrases, insulinases, invertases, isomerases, kinases, lactases, lipases, lipoxygenases, lysozymes, peroxidases, phosphatases, phospholipases, phosphorylases, proteinases and peptidases, recombinases, reverse transcriptases, telomerase, including RNA and/or protein components, and topoisomerases).

The preparation and use of the star polymers and loaded star polymers is further illustrated by the following examples.

EXAMPLES

Materials used in the following examples are listed in Table 1.

TABLE 1

| Abbreviation | Description | Company |
|---|---|---|
| MPEG-OH | Monomethyl End-capped Polyethylene Glycol (Mw = 5000 Da) | Fluka |
| VL | δ-Valerolactone | Sigma-Aldrich |
| 4-EtCH | 4-Ethylcyclohexanone | Sigma-Aldrich |
| 4-tBuCH | 4-tert-Butylcyclohexanone | Sigma-Aldrich |
| nBuCL | ε-Decalactone | Sigma-Aldrich |
| TBD | 1,5,7-Triazabicyclo[4.4.0]dec-5-ene | Sigma-Aldrich |
| BCH | 4,4'-Bicyclohexanone | TCI America |
| BA | Benzoic Acid | Sigma-Aldrich |
| Toluene | Toluene Anhydrous | Sigma-Aldrich |

Herein, Mn is the number average molecular weight, Mw is the weight average molecular weight, and MW is the molecular weight of one molecule. The term kDa refers to kiloDaltons (i.e. 1000 Daltons).

Monomethyl poly(ethylene glycol) (MPEG-OH), having a number average molecular weight of 5000 g/mol, PDI=1.02) obtained from Fluka, was purified azeotropically and recrystallized from benzene prior of use. 1,5,7-Triazabicyclo[4.4.0]dec-5-ene (TBD) was purified by sublimation, δ-valerolactone (VL) and -decalactone (nBuCL) were purified by vacuum distillation over $CaH_2$. Anhydrous toluene, benzoic acid (BA) and diethyl ether were used as received.

Methods of Analysis $^1$H NMR spectra were recorded on a Bruker Avance 2000 spectrometer operating at 400 MHz (proton) and were referenced to internal solvent (CDCl$_3$, $^1$H=7.26 ppm). All NMR spectra were recorded at room temperature using standard Bruker library pulse programs. All chemicals and solvents were purchased from Sigma-Aldrich Chemical Co (Milwaukee, Wis.), unless stated otherwise. Deuterated solvents were purchased from Cambridge Isotopes (Andover, Mass.) and used as received. Analytical gel permeation chromatography (GPC) was performed in THF using Waters high resolution columns HR1, HR2 and HR4E (flow rates 1 mL/min) and peaks detected using a Waters 996 diode array and a Waters 411 differential refractometer, calibrated using polystyrene standards to determine molecular weight and polydispersity index (PDI). Dynamic Light Scattering (LS) measurements yielded values for Mw and hydrodynamic radii ($R_H$) using the described GPC column set with a Wyatt DAWN EOS multi-angle light scattering detector.

Preparation of Monomers

γ-Ethyl-ε-caprolactone (EtCL) was synthesized from 4-ethylcyclohexanone according to the general procedure of Chang, M-Y., et al., Tetrahedron Letters, 2006, 47, 4865.

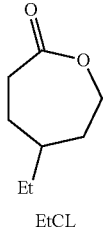

EtCL

γ-tert-Butyl-ε-caprolactone (tBuCL) was synthesized according to the procedure of Chang, M-Y., et al., Tetrahedron Letters, 2006, 47, 4865.

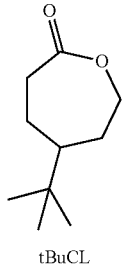

tBuCL

Bis-ε-caprolactone (BOD) was prepared from 4,4'-bicyclohexanone according to the procedure of Nijenhuis, A. J., et al., Polymer 1996, 37, 2783.

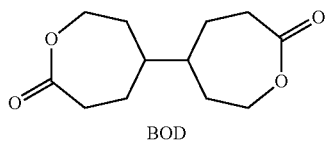

BOD

Preparation of Block-Copolymer Arms

Example 1

Synthesis of Diblock Copolymer ARM-1

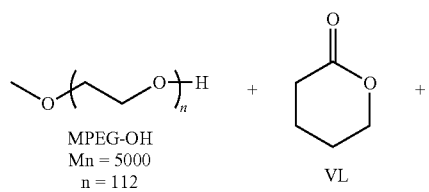

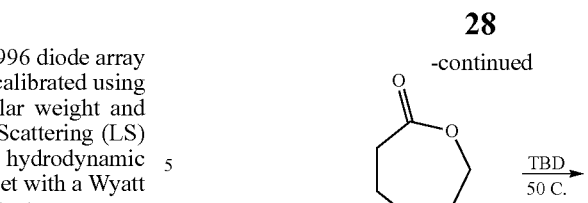

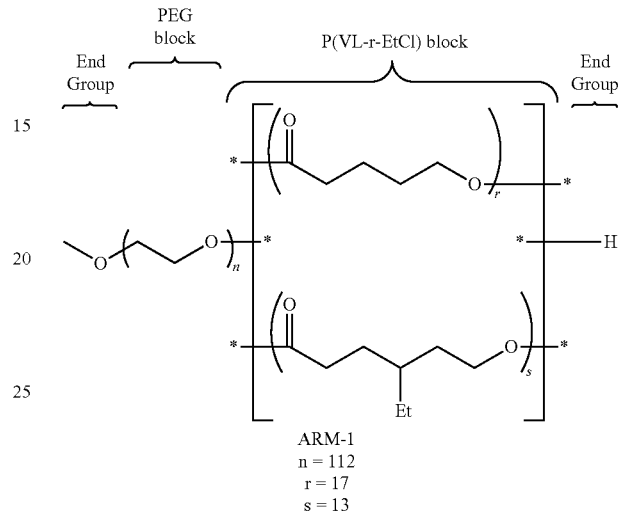

ARM-1
n = 112
r = 17
s = 13

The following procedure is representative. To a solution of MPEG-OH (0.3 g, 0.06 mmol) in anhydrous toluene (3.0 g), VL (0.18 g, 1.8 mmol), EtCL (0.26 g, 1.8 mmol) were added. To the obtained mixture, TBD (0.008 g, 0.06 mmol) was added. The reaction mixture was stirred for 2 hours at 50° C. and then the polymerization was quenched with benzoic acid. The resulting polymer solution was allowed to cool to room temperature. The polymer was precipitated from diethyl ether (75 mL), filtered and dried under vacuum at room temperature for 24 hours to give ARM-1 as a white amorphous powder (0.37 g, 50% yield). $^1$H NMR (CDCl$_3$, 400 MHz): δ (ppm)=4.14-4.00 (m, 60H, —CH$_2$O—), 3.64 (br s, 452H, —CH$_2$CH$_2$O), 3.38 (s, 3H, —OCH$_3$), 2.40-2.24 (m, 62H, —CH$_2$COO), 1.76-1.24 (m, 166H, CH$_2$CH$_2$CH$_2$O and CH$_2$CH(CH$_2$CH$_3$)CH$_2$CH$_2$O, 0.88 (t, 41H, CH$_3$CH$_2$); GPC (RI): Mn (PDI)=9.8 kDa (1.08), Mn ($^1$H NMR)=8.5 kDa (DP: VL=17, EtCL=13).

Example 2

Synthesis of Diblock Copolymer ARM-2

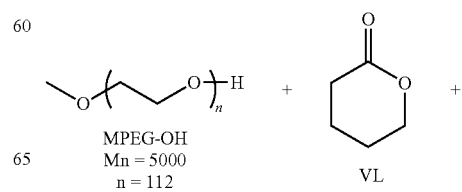

-continued

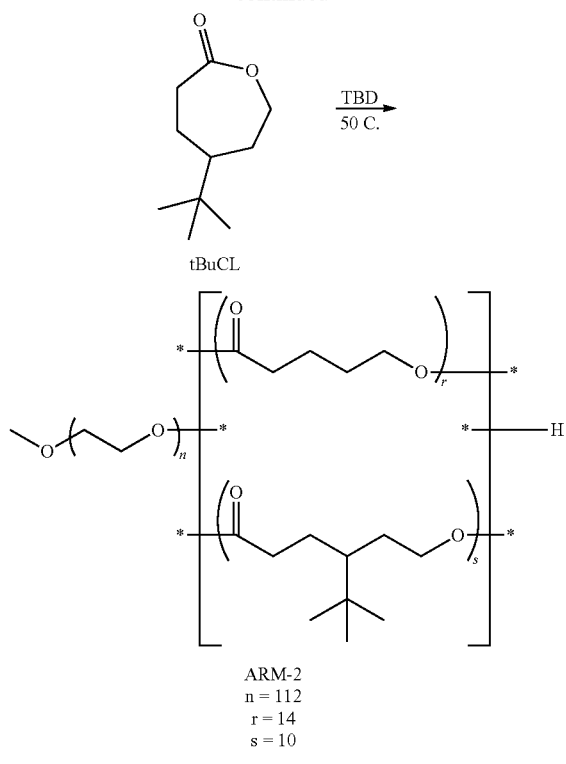

ARM-2
n = 112
r = 14
s = 10

To a solution of MPEG-OH (0.3 g, 0.06 mmol) in anhydrous toluene (3.0 g), VL (0.18 g, 1.8 mmol) and tBuCL (0.31 g, 1.8 mmol) were added. To the resulting solution, TBD (0.008 g, 0.06 mmol) was added. The mixture was stirred and allowed to react at 50° C. for 6 hours and then the polymerization was quenched with benzoic acid and allowed to cool to room temperature. The product was precipitated from diethyl ether (75 mL), filtered, and dried under vacuum at room temperature for 24 hours to give ARM-2 as a white amorphous powder (0.42 g, 53% yield). $^1$H NMR (CDCl$_3$, 400 MHz): δ (ppm)=4.12-3.92 (m, 48H, 3.64, —CH$_2$O—, (br s, 452H, —CH$_2$CH$_2$O—), 3.38 (s, 3H, —OCH$_3$), 2.50-2.14 (m, 52H, —CH$_2$COO), 1.90-1.24 (m, 105H, —CH$_2$CH$_2$CH$_2$O and CH$_2$CH(C(CH$_3$)$_3$)CH$_2$CH$_2$O), 0.88 (s, 89H, —C(CH$_3$)$_3$); GPC (RI): Mn (PDI)=10.6 kDa (1.23), Mn ($^1$H NMR)=8.1 kDa (DP: VL=14, tBuCL=10).

Example 3

Synthesis of Diblock Copolymer ARM-3

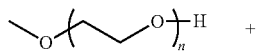

MPEG-OH
Mn = 5000
n = 112

-continued

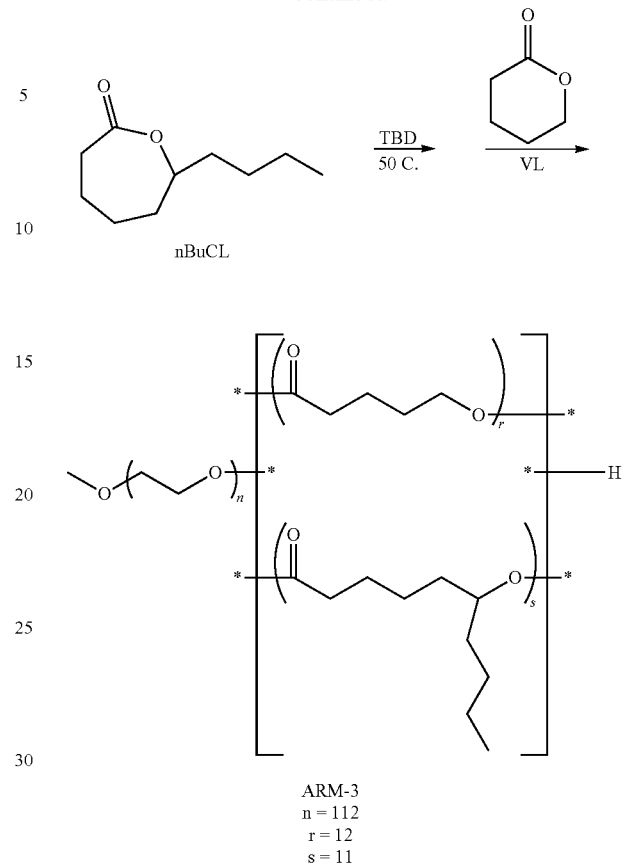

ARM-3
n = 112
r = 12
s = 11

To a solution of MPEG-OH (0.3 g, 0.06 mmol, 5 kDa) in anhydrous toluene (3.0 g), g-decalactone (nBuCL, 0.612 g, 3.6 mmol) and TBD (0.005 g, 0.036 mmol) were added. The reaction was allowed to stir for 5 hours at 50° C., then VL (0.12 g, 1.2 mmol) was added to the reaction mixture and stirring continued for an additional hour. The nBuCl was slow to polymerize due to steric hindrance. The staggered addition of VL produces a tapered polyester block having a higher concentration of nBuCL repeat units near the PEG block and a more random distribution of nBuCl and VL repeat units near the core. Upon completion, the polymerization was quenched with benzoic acid in CHCl$_3$ (0.1 wt %). The product was precipitated using diethyl ether (75 mL), filtered and dried under vacuum at room temperature for 24 hours, giving ARM-3 as a white amorphous powder (0.26 g, 25%). $^1$H NMR (CDCl$_3$, 400 MHz): δ (ppm)=4.2-4.10 (m, 47H, —CH$_2$O—), 3.64 (br s, 452H, —CH$_2$CH$_2$O), 3.38 (s, 3H, —OCH$_3$), 2.40-2.24 (m, 45H, —CH$_2$COO), 1.82-1.14 (m, 194H, —CH$_2$CH$_2$CH$_2$O— and CH$_2$CH(CH$_2$CH$_3$)CH$_2$CH$_2$O, 0.91 (t, 34H, CH$_3$(CH$_2$)$_3$—; GPC (RI): Mn (PDI)=10.8 kDa (1.2), Mn ($^1$H NMR)=8.1 kDa (DP: VL=12, nBuCL=11).

Example 4 (Comparative)

Synthesis of Diblock Copolymer ARM-4

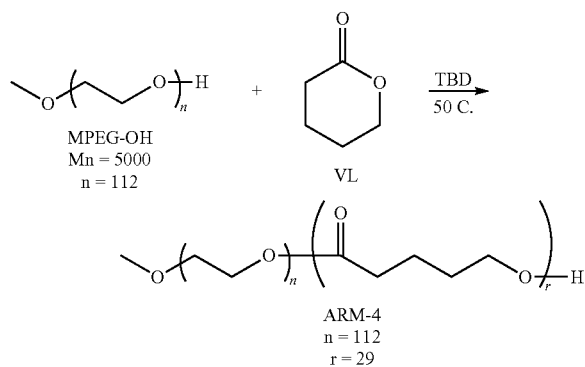

ARM-4 was prepared according to the general procedure of Example 1 using MPEG-OH (2.0 g, 0.4 mmol, 5 kDa), anhydrous toluene (9.5 g), valerolactone (VL, 1.2 g, 12.0 mmol) and TBD (0.00865 g, 62.2 μmol). $^1$H NMR (CDCl$_3$, 400 MHz): δ (ppm)=4.09 (tr, 57H, —CH$_2$—CH$_2$—OOC—), 3.66 (br, 452H, —O—CH$_2$—CH$_2$—O—), 3.39 (s, 3H—OCH$_3$), 2.35 (tr, 59H, —CH$_2$—CH$_2$—COO—), 1.70 (br, 112H, —OOC—CH$_2$—CH$_2$—CH$_2$—CH$_2$—OOC—) GPC (RI): Mn (PDI)=9.8 kDa (1.08), Mn ($^1$H NMR)=7.9 kDa (DP: VL=29).

Example 5 (Comparative)

Synthesis of ARM-5

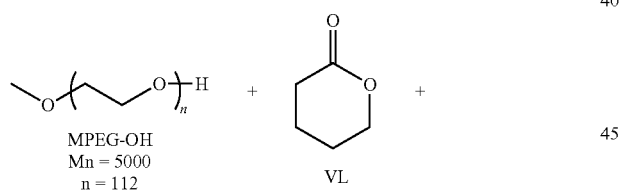

ARM-5 was prepared according to the general procedure of Example 1 using MPEG-OH (1.5 g, 0.3 mmol, 5 kDa), anhydrous toluene (15.0 g), valerolactone (VL, 0.9 g, 9.0 mmol), caprolactone (CL, 1.26 g, 9.0 mmol), and TBD (0.1 g, 0.72 mmol). $^1$H NMR (CDCl$_3$, 400 MHz): δ (ppm)=4.09 (tr, 51H, —CH$_2$—CH$_2$—OOC—), 3.66 (br, 450H, —O—CH$_2$—CH$_2$-0-), 3.39 (s, 3H—OCH$_3$), 2.35 (tr, 50H, —CH$_2$—CH$_2$—COO—), 1.68 (br, 107H, —OOC—CH$_2$—CH$_2$—CH$_2$—CH$_2$—OOC— and —OOC—CH$_2$—CH$_2$—CH$_2$—CH$_2$—CH$_2$—OOC, 1.35 (br 23H, —OOC—CH$_2$—CH$_2$—CH$_2$—CH$_2$—OOC)). GPC (RI): Mn (PDI)= 9.6 kDa (1.27), Mn ($^1$H NMR)=7.70 kDa (DP: VL=13, CL=12).

Preparation of Nanogel Core Star Polymers with Block-Copolymer Arms

Example 6

Synthesis of Nanogel Star Polymer SP-1 Using ARM-1

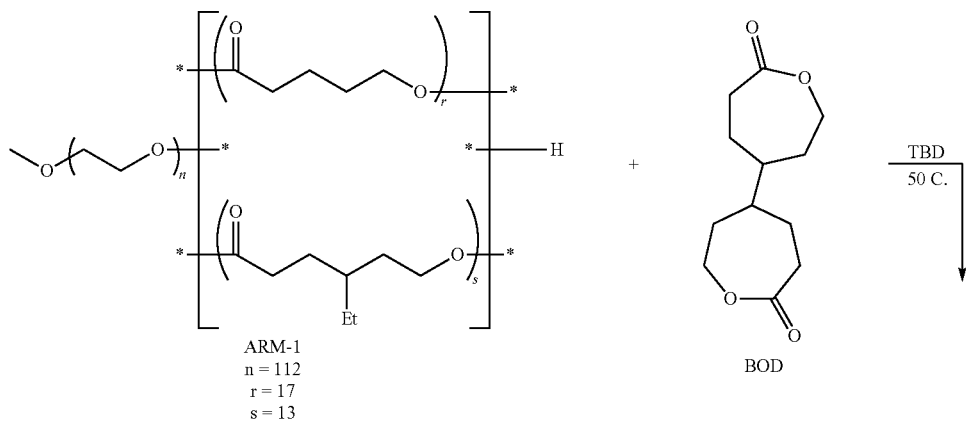

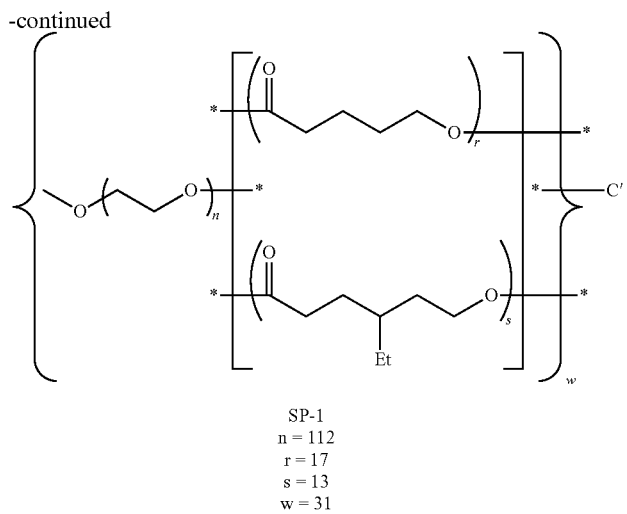

SP-1
n = 112
r = 17
s = 13
w = 31

C' in the above structure of SP-1 represents the cross-linked polyester core derived from BOD. Subscript w is the average number of arms of SP-1 (i.e., C' has a valency of w). The following procedure is representative. ARM-1 (0.94 g, 0.11 mmol, Mn ($^1$H-NMR)=8.5 kDa) was dissolved in anhydrous toluene (5.5 g). BOD (0.19 g, 0.84 mmol) was added to the reaction mixture followed by the addition of TBD (0.10 g of 5 wt % solution in anhydrous toluene). The reaction mixture was allowed to stir for 16 hours in a glove box at ambient temperature. Upon completion of the reaction, the mixture was quenched with a solution of benzoic acid in CHCl$_3$ (0.1 wt %). The product was precipitated into cold diethyl ether, filtered and dried under vacuum for 24 hours. The crude star polymer was dissolved in 4 mL of dichloromethane (DCM) and the resulting solution was filtered through a 1 μm glass syringe filter. Diethyl ether (about 15 mL) was slowly added to the stirred solution. The resulting cloudy solution was allowed to settle until the formation of transparent oil was observed at the bottom of the flask. The solution was decanted off. The remaining oil was dissolved in a minimum amount of DCM and precipitated using diethyl ether. The solid product was filtered and dried under vacuum for 24 hours, giving SP-1 as a white amorphous powder (0.56 g, 59% yield). $^1$H NMR (CDCl$_3$, 400 MHz): δ (ppm)=4.18-4.00 (m, 64H, —CH$_2$O—), 3.64 (br s, 452H, —CH$_2$CH$_2$O—), 3.38 (s, 3H, —OCH$_3$), 2.40-2.21 (m, 75H, —CH$_2$COO), 1.84-1.22 (m, 277H, —CH$_2$CH$_2$CH$_2$O— and —CH$_2$CH(CH$_2$CH$_3$)CH$_2$CH$_2$O—), 0.88 (t, 44H, —CH$_2$CH$_3$); GPC (by refractive index (RI)): Mn (PDI)=84.5 kDa (1.20), R$_H$ (THF)=6.2 nm, Mw (by light scattering (LS))=315 kDa, number of arms=31.

Example 7

Synthesis of Star Polymer SP-2 Using ARM-2

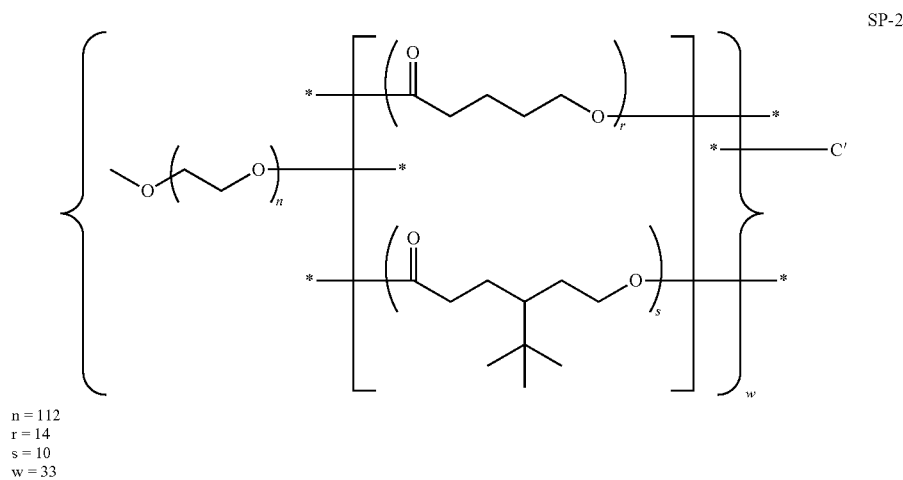

SP-2
n = 112
r = 14
s = 10
w = 33

ARM-2 (0.89 g, 0.11 mmol, Mn ($^1$HNMR)=7.8 kDa) was dissolved in anhydrous toluene (5.5 g). BOD (0.19 g, 0.84 mmol) was added to the reaction mixture followed by the addition of TBD (0.10 g of 5 wt % solution in anhydrous toluene). The reaction mixture was allowed to stir for 16 hours in a glove box at ambient temperature. Upon completion of the reaction, the mixture was quenched with solution of benzoic acid in CHCl$_3$ (0.1 wt %). The product was precipitated into cold diethyl ether, filtered, and dried under vacuum for 24 hours. The crude star polymer was then dissolved in DCM (4 mL) and filtered through a 1 m glass syringe filter. Diethyl ether (about 15 mL) was slowly added to the stirred solution. The resulting cloudy solution was allowed to settle until the formation of a transparent oil at the bottom of the flask was observed. The solution was decanted off. The remaining oil was dissolved in a minimum amount of DCM, precipitated from diethyl ether, filtered, and dried under vacuum for 24 hours, giving SP-2 as a white waxy solid (0.30 g, 36% yield). $^1$H NMR (CDCl$_3$, 400 MHz): δ (ppm)=4.10-3.96 (m, 50H, —CH$_2$O—), 3.64 (br s, 452H, —CH$_2$CH$_2$O—), 3.38 (s, 3H, —OCH$_3$), 2.50-2.15 (m, 76H, —CH$_2$COO), 1.98-1.25 (m, 105H, —CH$_2$CH$_2$CH$_2$O— and —CH$_2$CH(C(CH$_3$))CH$_2$CH$_2$—), 0.89 (s 84H, (CH$_3$)$_3$C—) GPC (RI): Mn (PDI)=81.5 kDa (1.3), hydrodynamic diameter R$_H$ (THF)=6.1, Mw (LS)=257 kDa, number of arms=33.

Example 8

Synthesis of Star Polymer SP-3 Using Diblock Copolymer ARM-3

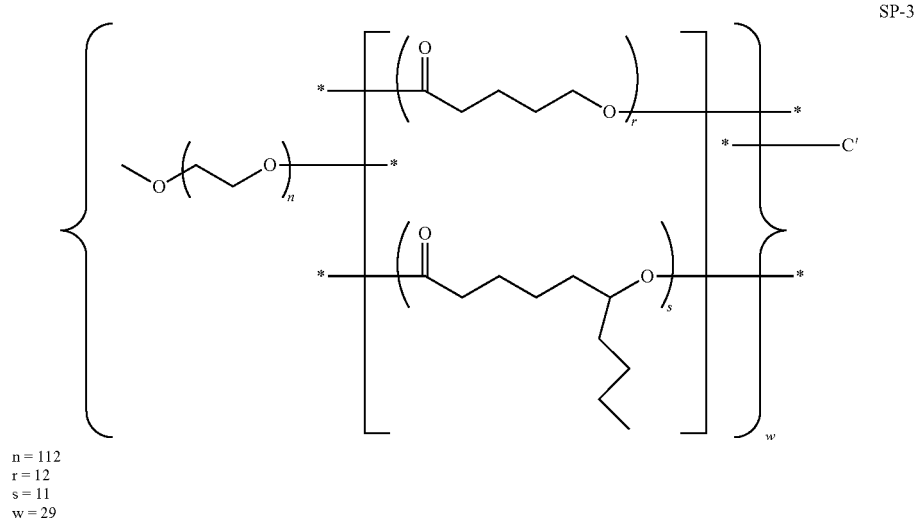

n = 112
r = 12
s = 11
w = 29

ARM-3 (0.87 g, 0.11 mmol, M$_n$($^1$HNMR)=8.1 kDa) was dissolved in anhydrous toluene (5.5 g). BOD (0.19 g, 0.84 mmol) was added to the reaction mixture followed by the addition of TBD (0.10 g of 5 wt % solution in anhydrous toluene). The reaction mixture was allowed to stir for 16 h in a glove box at 50° C. Upon completion of the reaction, the mixture was quenched with solution of benzoic acid in CHCl$_3$ (0.1 wt %) and the solution was precipitated into cold diethyl ether, filtered and dried under vacuum for 24 hours. The crude star polymer was then dissolved in DCM (4 mL), filtered through a 1 μm glass syringe filter. Diethyl ether (about 15 mL) was slowly added to a stirred solution. The resulting cloudy solution was allowed to settle until the formation of transparent oil at the bottom of the flask was observed. The solution was decanted off and the oil was dissolved in a minimum amount of DCM, precipitated from diethyl ether, filtered and dried under vacuum for 24 hours, giving SP-3 as a white waxy solid: (0.26 g, 25% yield). $^1$H NMR (CDCl$_3$, 400 MHz): δ (ppm)=4.17-4.04 (m, 49H, —CH$_2$O—), 3.64 (br s, 453H, —CH$_2$CH$_2$O), 3.38 (s, 3H, —OCH$_3$), 2.40-2.24 (m, 47H, —CH$_2$COO), 1.82-1.14 (m, 227H, —CH$_2$CH$_2$CH$_2$O— and CH$_2$CH(CH$_2$CH$_3$)CH$_2$CH$_2$O), 0.91 (t, 35H, CH$_3$(CH$_2$)$_3$—; GPC (RI) where RI is refractive index: Mn (PDI)=106 kDa (1.25), Mw (LS)= 235 kDa, number of arms=29.

Example 9

Synthesis of Star Polymer SP-4 Using Diblock Copolymer ARM-4

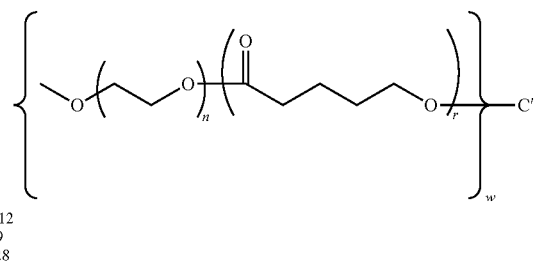

n = 112
r = 29
w = 28

SP-4 was prepared according to the general procedure of Example 6 using ARM-4 (0.87 g, 0.11 mmol based on Mn ($^1$HNMR)=7.9 kDa), anhydrous toluene (5.5 g), BOD (0.19 g, 0.84 mmol) and TBD (0.10 g of 5 wt % solution in anhydrous toluene. $^1$H NMR: (CDCl$_3$, 400 MHz): δ (ppm)= 4.09 (br, 84H, —CH$_2$—CH$_2$—OOC—), 3.66 (br, 452H, —O—CH$_2$—CH$_2$-0-), 3.39 (s, 3H —OCH$_3$), 2.35 (tr, 84H, —CH$_2$—CH$_2$—COO—), 1.70 (br, 160H, —OOC—CH$_2$—CH$_2$—CH$_2$—CH$_2$—OOC—). GPC(RI): Mn (PDI)=69.2 kDa (1.2), Mw (LS)=221 kDa, number of arms=29.

Example 10

Synthesis of Star Polymer SP-5 Using ARM-5

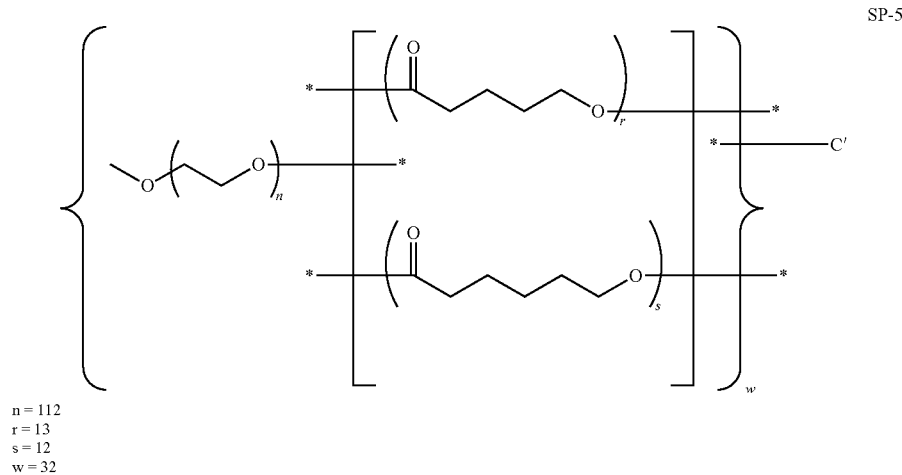

n = 112
r = 13
s = 12
w = 32

Table 2 summarizes the star polymers formed. The degree of polymerization (DP) of each lactone monomer of the arm is shown in parentheses next to the monomer name. $R_H$ is the hydrodynamic radius in nanometers. AAN is the average number of arms per star polymer macromolecule. The "# blocks" (number of blocks) of the arm includes the PEG block. It should be understood that the PEG block has a DP of 112. The arms of SP-1, SP-2, and SP-5 have one polyester block, which is a random copolymer block. SP-4 has one polyester block, which is a homopolymer (SP-4). SP-3 has one polyester block which has gradient distribution of the repeat units due to the difference in reactivities of VL and nBuCL.

(approximately 3 hours) to remove the organic solvent residue and was filtered through 0.4 m Nylon filter. The filtered solution was analyzed by UV-Vis to determine the drug loading (DL) as wt % drug based on the initial weight of star polymer and encapsulation efficiencies (EE) as % of initial drug loaded.

Examples 12-15

Loaded star polymers LSP-2 to LSP-5 were prepared following the procedure of Example 11 using SP-2 to SP-5, respectively, and CoQ10.

TABLE 2

| Example | Star Polymer Name | Arm Monomer(s) (DP) | # Blocks | Mn, kDa (PDI) | Star Polymer Mn, kDa | Mw, kDa (PDI) | $R_H$, nm | AAN |
|---|---|---|---|---|---|---|---|---|
| 6 | SP-1 | VL(17), EtCL(13) | 2 | 8.1 (1.2) | 242 | 315 (1.3) | 6.2 | 37 |
| 7 | SP-2 | VL(14), tBuCL(10) | 2 | 7.8 (1.2) | 198 | 257 (1.3) | 6.1 | 33 |
| 8 | SP-3 | VL(12), nBuCL(11) | 2 | 8.1 (1.2) | 214 | 235 (1.1) | 5.7 | 29 |
| 9 | SP-4 | VL(29) | 2 | 7.9 (1.1) | 184 | 221 (1.2) | 5.5 | 28 |
| 10 | SP-5 | VL(13), CL(12) | 2 | 7.7 (1.1) | 207 | 248 (1.2) | 5.9 | 32 |

Preparation of Loaded Star Polymers

The nanogel core star polymers were loaded with various amounts of Coenzyme Q10 (CoQ10), a model hydrophobic dietary supplement and cargo. A representative procedure follows.

Example 11

Preparation of loaded star polymer LSP-1 using star polymer SP-1 and CoQ10. Stock solutions of star polymer SP-1 and CoQ10 were prepared separately in anhydrous THF and combined to form a solution containing star polymer (20 mg) and CoQ10 (2 mg, initially 10 wt % of the initial weight of the star polymer) in THF (0.2 mL). Water (4 mL) was rapidly added to the homogeneous solution while stirring. The resulting solution was sparged with $N_2$

Examples 16-17

Loaded star polymers LSP-6 to LSP-7 were prepared following the general procedure of Example 11 using SP-2 and SP-3, respectively, and an initial CoQ10 amount equal to 30 wt % of the initial weight of the star polymer.

Table 3 summarizes the loaded star polymers formed. Initial CoQ10 weight percent (wt %)=100%×(initial weight of CoQ10)/(initial weight of star polymer). Loaded CoQ10 wt %=100%×(weight of loaded CoQ10 measured by UV-Vis)/(initial weight of star polymer). Encapsulation efficiency (EE %)=100%×(weight of loaded CoQ10)/(initial weight of CoQ10).

TABLE 3

| Example | Loaded Star Polymer Name | Star Polymer | Arm Monomer(s) (DP) | Initial CoQ10 (wt %) | Loaded CoQ10 (wt %) | EE (%) |
|---|---|---|---|---|---|---|
| 11 | LSP-1 | SP-1 | VL(17), EtCL(13) | 10 | 7.6 | 76 |
| 12 | LSP-2 | SP-2 | VL(14), tBuCL(10) | 10 | 9.2 | 92 |
| 13 | LSP-3 | SP-3 | VL(12), nBuCL(11) | 10 | 8.1 | 81 |
| 14 | LSP-4 | SP-4 | VL(29) | 10 | 4.9 | 49 |
| 15 | LSP-5 | SP-5 | VL(13), CL(12) | 10 | 5.1 | 51 |
| 17 | LSP-6 | SP-2 | VL(14), tBuCL(10) | 30 | 27 | 90 |
| 16 | LSP-7 | SP-3 | VL(12), nBuCL(11) | 30 | 12 | 40 |

Figure 3:
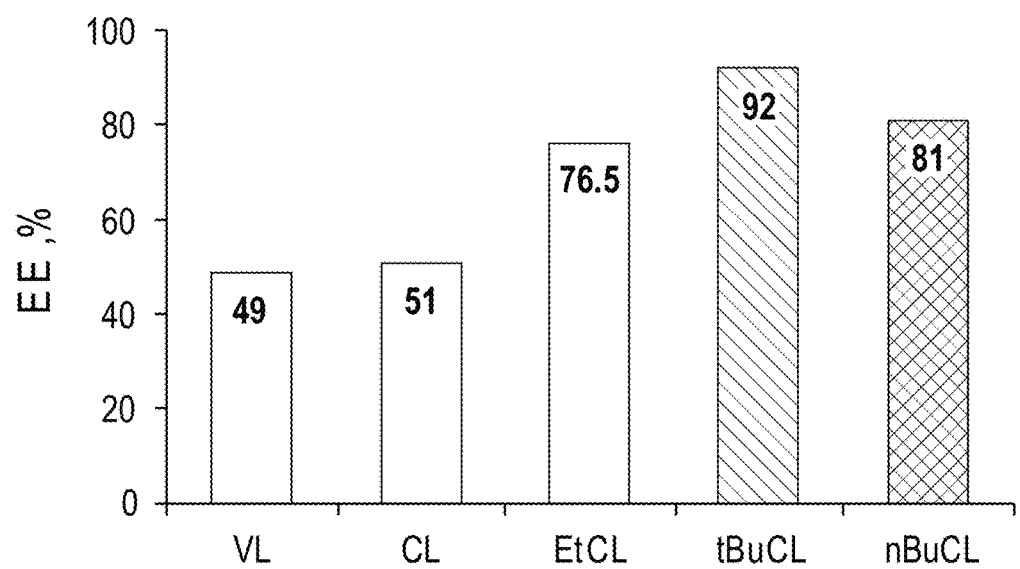
FIG. 3 is a bar graph comparing CoQ10 encapsulation efficiencies (EE %) of various loaded star polymers differing in the pendent alkyl chain of the polyester block of the arms, where the initial amount of CoQ10 used was 10 wt % based on the initial star polymer weight.

The results indicate the pendent alkyl functionality of the polyester block of the star polymer arm significantly affects CoQ10 loading. For example, star-polymer SP-4, whose arms have a polyester block solely comprised of δ-valerolactone (VL) units, demonstrated low encapsulation efficiency (49%) when the initial CoQ10 amount was 10 wt % based on weight of the star polymer. Replacement of half of the VL units with more hydrophobic ε-caprolactone (CL) moieties resulted in marginal improvement in encapsulation efficiency (51%) at initial CoQ10=10 wt %. However, when about 50% of the VL units were replaced with γ-ethyl ε-caprolactone (EtCL), the encapsulation efficiency increased to 76.5% for initial CoQ10=10 wt %. When the pendent ethyl functionality was extended to butyl (half of the VL units were replaced with ε-decalactone (nBuCL)) the encapsulation efficiency was 81% for initial CoQ10=10 wt %. When the n-butyl functionality was replaced with t-butyl (50% of VL units in the core were replaced with tert-butyl caprolactone (tBuCL)), the encapsulation efficiency rose to approximately 92% for initial CoQ10=10 wt %. FIG. 3 is a bar graph summarizing the encapsulation efficiencies obtained with the different lactone monomers.

Figure 4:
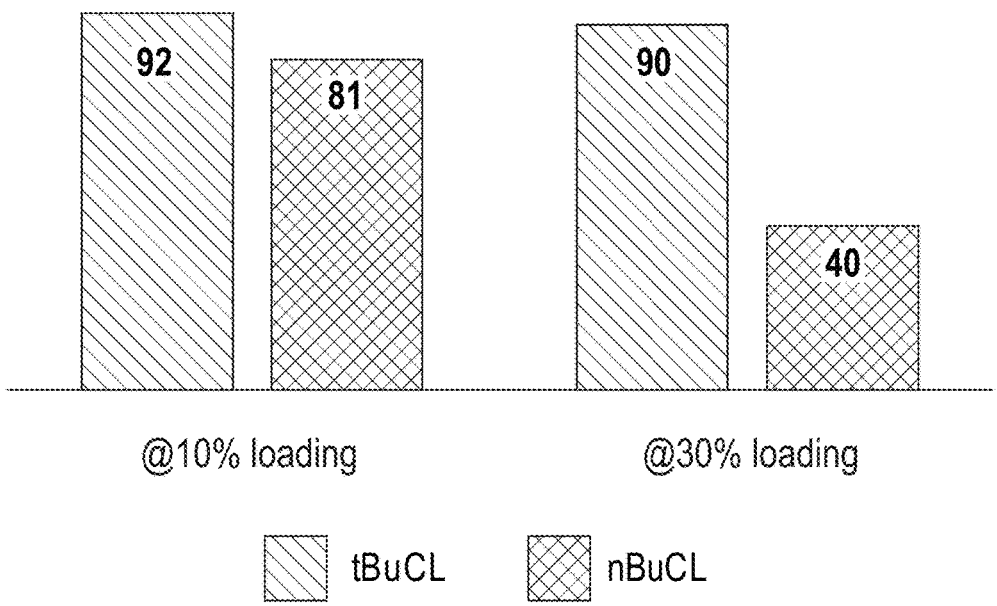
FIG. 4 is a bar graph comparing CoQ10 encapsulation efficiencies (EE %) of loaded star polymers LSP-6 (t-butyl side chain) and LSP-7 (n-butyl side chain), where the initial amount of CoQ10 was 30 wt % based on the initial star polymer weight.

Without wishing to be bound by theory, the results indicate that reduced crystallinity and increased surface area of the hydrophobic block of the arms appears to be a main factor influencing cargo loading levels. A comparison of cargo loading efficiencies for nBuCL- and tBuCL-containing star polymers supports this hypothesis. Although both star polymers have the same number of carbon atoms in the pendent alkyl group and therefore have almost equivalent hydrophobicity values, the topology of the pendent alkyl chain has a significant effect on encapsulation efficiency. Thus, the tert-butyl pendent functionality, which is more sterically demanding, disrupts the tight packing of the core region to a greater extent than the n-butyl group, creating a larger surface area for favored interactions with the hydrophobic cargo CoQ10. The effect of increased surface area became especially apparent when the initial CoQ10 loading level was increased to 30 wt % (FIG. 4, bar graph). At 30 wt % initial CoQ10, the EE % for the loaded star polymer LSP-6 containing the tert-butyl group remained high (90%), whereas the EE % of the loaded star polymer LSP-7 having the n-butyl group decreased to 40%.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

When a range is used to express a possible value using two numerical limits X and Y (e.g., a concentration of X ppm to Y ppm), unless otherwise stated the value can be X, Y, or any number between X and Y.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

What is claimed is:

1. A nanogel star polymer, comprising:
a crosslinked hydrophobic polyester core C'; and
6 to 50 independent linear block copolymer arms, each of the arms comprising i) a hydrophilic PEG block P' comprising a poly(ethylene oxide) chain and ii) a hydrophobic polyester block P''', a first end unit of the polyester block linked to the PEG block, a second end unit of the polyester block linked to the core C', wherein the polyester block P''' comprises an ester repeat unit of structure

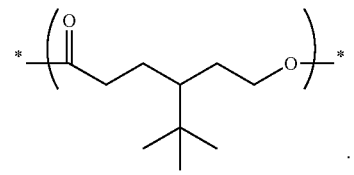

2. The nanogel star polymer of claim 1, wherein the polyester block comprises a second ester repeat unit selected from the group consisting of:

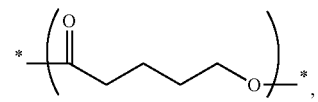

and

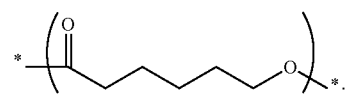

3. The nanogel star polymer of claim 2, wherein the second ester repeat unit is

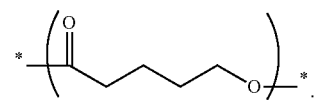

4. The nanogel star polymer of claim 2, wherein the second ester repeat unit is

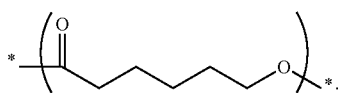

5. The nanogel star polymer of claim 1, wherein the star polymer comprises 20 to 40 of the arms.

6. The nanogel star polymer of claim 1, wherein the PEG block has a number average molecular weight Mn of about 1,000 to about 10,000.

7. The nanogel star polymer of claim 1, wherein a second end of the PEG block is covalently linked to an alkoxy end group.

8. The nanogel star polymer of claim 1, wherein the polyester block P'" of the arm is a random copolymer of the ester repeat unit and a second ester repeat unit.

9. The nanogel star polymer of claim 1, wherein the polyester block of the arm is a block copolymer chain comprising a first polyester block comprising the ester repeat unit and a second polyester block comprising a second ester repeat unit.

10. The nanogel star polymer of claim 9, wherein the first polyester block is located between, and covalently linked to, both the PEG block and the second polyester block, and the second polyester block is linked to the core C'.

11. The nanogel star polymer of claim 9, wherein the second polyester block is located between, and covalently linked to, both the PEG block and the first polyester block, and the first polyester block is linked to the core C'.

12. A loaded star polymer, comprising:
the nanogel star polymer of claim 1; and
a hydrophobic therapeutic agent used in treatment of cellular tissue;
wherein
the therapeutic agent is in contact with the polyester block P'" and/or the core.

13. The loaded star polymer of claim 12, wherein the hydrophobic therapeutic agent is bound by non-covalent interactions to the polyester block of the arms of the star polymer.

14. The loaded star polymer of claim 12, wherein the hydrophobic therapeutic agent is present in the loaded star polymer in the amount of 5-30 wt % based on weight of the star polymer.

15. The loaded star polymer of claim 12, wherein the hydrophobic therapeutic agent is a drug used to treat a medical condition.

16. The loaded star polymer of claim 12, wherein the hydrophobic therapeutic agent is an imaging agent used in diagnosing a medical condition.

17. The loaded star polymer of claim 12, wherein the hydrophobic therapeutic agent is a dietary supplement.

18. The loaded star polymer of claim 17, wherein the dietary supplement is selected from the group consisting of CoQ10 (ubiquinone), ubiquinol, and combinations thereof.

19. The loaded star polymer of claim 12, wherein the loaded star polymer is capable of delivery to cellular tissue by injection and/or oral ingestion.

20. An aqueous mixture comprising the loaded star polymer of claim 12, wherein the loaded star polymer is present as a particle in contact with water.

21. The aqueous mixture of claim 20, wherein the particle has an average circular diameter of 2 nm to 500 nm.

* * * * *